(12) United States Patent
Belov et al.

(10) Patent No.: US 8,980,093 B2
(45) Date of Patent: Mar. 17, 2015

(54) MULTICAPILLARY DEVICE FOR SAMPLE PREPARATION

(76) Inventors: Yuri P. Belov, State College, PA (US);
Carlo G. Pentano, Pennsylvania Furnace, PA (US); Ksenia Lvova, State College, PA (US)

( * ) Notice: Subject to any disclaimer, the term of this patent is extended or adjusted under 35 U.S.C. 154(b) by 198 days.

(21) Appl. No.: 13/015,400

(22) Filed: Jan. 27, 2011

(65) Prior Publication Data

US 2011/0263838 A1    Oct. 27, 2011

Related U.S. Application Data

(63) Continuation of application No. 11/524,426, filed on Sep. 20, 2006, which is a continuation-in-part of application No. 10/955,377, filed on Sep. 30, 2004, now Pat. No. 7,166,212.

(60) Provisional application No. 60/507,474, filed on Sep. 30, 2003.

(51) Int. Cl.
*G01N 30/56* (2006.01)
*G01N 30/60* (2006.01)

(52) U.S. Cl.
CPC ............ *G01N 30/56* (2013.01); *G01N 30/6043* (2013.01); *G01N 30/6078* (2013.01); *G01N 2030/567* (2013.01)
USPC ... 210/635; 210/656; 210/198.2; 210/500.23; 210/502.1

(58) Field of Classification Search
CPC .......... G01N 30/6043; G01N 30/6078; G01N 2030/567; G01N 30/56

USPC .............. 210/198.2, 635, 656, 500.23, 502.1; 96/101; 422/70, 100, 101; 536/25.4
See application file for complete search history.

(56) References Cited

U.S. PATENT DOCUMENTS

| | | | |
|---|---|---|---|
| 3,570,673 A | 3/1971 | Dutz et al. |
| 4,043,905 A | 8/1977 | Novotny et al. |
| 4,045,352 A | 8/1977 | Rembaum et al. |
| 4,214,020 A | 7/1980 | Ward et al. |
| 4,293,413 A | 10/1981 | Schnell |
| 4,293,415 A | 10/1981 | Bente, III et al. |
| 4,424,127 A | 1/1984 | Roeraade |
| 4,654,265 A | 3/1987 | Kamei et al. |
| 4,657,742 A | 4/1987 | Beaver |

(Continued)

FOREIGN PATENT DOCUMENTS

| | | |
|---|---|---|
| CH | 654666 | 2/1986 |
| DE | 4443754 | 6/1996 |

(Continued)

OTHER PUBLICATIONS

Alltech Multi-Cap Capillary Column, Bulletin #356, Alltech Inc., 1997.

(Continued)

*Primary Examiner* — Ernest G Therkorn
(74) *Attorney, Agent, or Firm* — Vinnovations Law, PLLC

(57) ABSTRACT

A multicapillary sample preparation device, especially useful for handling biological samples, comprising a plurality of uniform capillary tubes coated with a stationary phase, and arranged in a monolithic element. The multicapillary device is suitable for attachment to a pipette, micropipette, syringe, or other analytical or sample preparation instrument.

26 Claims, 25 Drawing Sheets

(56) References Cited

U.S. PATENT DOCUMENTS

| | | |
|---|---|---|
| 4,689,267 A | 8/1987 | Takamizawa et al. |
| 4,715,105 A | 12/1987 | Beaver |
| 4,818,264 A | 4/1989 | Langhorst |
| 4,957,620 A * | 9/1990 | Cussler .................. 210/635 |
| 4,999,164 A | 3/1991 | Puchinger et al. |
| 5,092,155 A | 3/1992 | Rounbehler et al. |
| 5,092,219 A | 3/1992 | Rounbehler et al. |
| 5,154,822 A | 10/1992 | Simpson et al. |
| 5,160,627 A * | 11/1992 | Cussler et al. ............ 210/639 |
| 5,194,333 A | 3/1993 | Ohnaka et al. |
| 5,362,859 A | 11/1994 | Zale |
| 5,395,521 A | 3/1995 | Jagadeeswaran |
| 5,429,746 A | 7/1995 | Shadie et al. |
| 5,438,127 A | 8/1995 | Woodard et al. |
| 5,460,781 A | 10/1995 | Hori et al. |
| 5,552,047 A | 9/1996 | Oshida et al. |
| 5,578,204 A | 11/1996 | Bartholmes et al. |
| 5,610,290 A | 3/1997 | Woodard et al. |
| 5,616,701 A | 4/1997 | Woodard et al. |
| 5,683,916 A | 11/1997 | Goffe et al. |
| 5,774,779 A | 6/1998 | Tuchinskiy |
| 5,851,491 A | 12/1998 | Moulton |
| 5,876,918 A * | 3/1999 | Wainwright et al. ............ 435/4 |
| 6,007,609 A | 12/1999 | Semerdjian et al. |
| 6,045,757 A | 4/2000 | Moriarty et al. |
| 6,048,457 A | 4/2000 | Kopaciewicz et al. |
| 6,117,394 A | 9/2000 | Smith |
| 6,123,905 A | 9/2000 | Torti et al. |
| 6,143,252 A | 11/2000 | Haxo, Jr. et al. |
| 6,162,341 A | 12/2000 | Nordman et al. |
| 6,168,948 B1 | 1/2001 | Anderson et al. |
| 6,174,352 B1 | 1/2001 | Semerdjian et al. |
| 6,174,673 B1 | 1/2001 | Short et al. |
| 6,207,049 B1 | 3/2001 | Abdel-Rahman |
| 6,231,739 B1 | 5/2001 | Nordman et al. |
| 6,270,674 B1 | 8/2001 | Baurmeister et al. |
| 6,306,659 B1 | 10/2001 | Parce et al. |
| 6,309,828 B1 | 10/2001 | Schleifer et al. |
| 6,325,114 B1 | 12/2001 | Bevirt et al. |
| 6,329,209 B1 | 12/2001 | Wagner et al. |
| 6,333,088 B1 | 12/2001 | Le Febre et al. |
| 6,338,802 B1 | 1/2002 | Bodner et al. |
| 6,357,484 B1 | 3/2002 | Semerdjian et al. |
| 6,387,236 B2 | 5/2002 | Nordman et al. |
| 6,387,331 B1 | 5/2002 | Hunter |
| 6,406,921 B1 | 6/2002 | Wagner et al. |
| 6,416,716 B1 | 7/2002 | Shukla et al. |
| 6,451,260 B1 | 9/2002 | Dusterhoft et al. |
| 6,482,362 B1 | 11/2002 | Smith |
| 6,537,502 B1 | 3/2003 | Shukla et al. |
| 6,566,145 B2 | 5/2003 | Brewer |
| 6,576,478 B1 | 6/2003 | Wagner et al. |
| 6,582,969 B1 | 6/2003 | Wagner et al. |
| 6,596,237 B1 | 7/2003 | Borrelli et al. |
| 6,596,545 B1 | 7/2003 | Wagner et al. |
| 6,635,201 B1 | 10/2003 | Kopaciewicz et al. |
| 6,638,482 B1 | 10/2003 | Ackley et al. |
| 6,640,588 B2 | 11/2003 | Semerdjian |
| 6,743,633 B1 | 6/2004 | Hunter |
| 6,759,126 B1 | 7/2004 | Malik et al. |
| 6,780,314 B2 | 8/2004 | Jinno et al. |
| 6,780,582 B1 | 8/2004 | Wagner et al. |
| 6,794,127 B1 | 9/2004 | Lafferty et al. |
| 6,830,717 B2 | 12/2004 | Kopaciewicz et al. |
| 6,866,824 B2 | 3/2005 | Lafferty et al. |
| 6,870,165 B2 | 3/2005 | Amirkhanian et al. |
| 6,875,354 B1 | 4/2005 | Kopaciewicz et al. |
| 6,886,824 B2 | 5/2005 | Johdai et al. |
| 6,972,183 B1 | 12/2005 | Lafferty et al. |
| 6,992,181 B2 | 1/2006 | Tooke et al. |
| 7,118,657 B2 | 10/2006 | Golovchenko et al. |
| 7,118,671 B2 | 10/2006 | Kumakhov et al. |
| 7,122,640 B2 | 10/2006 | Gjerde et al. |
| 7,151,167 B2 | 12/2006 | Gjerde et al. |
| 7,166,212 B2 * | 1/2007 | Belov et al. ............ 210/198.2 |
| 7,208,072 B2 | 4/2007 | Amirkhanian et al. |
| 7,247,469 B2 | 7/2007 | Wagner et al. |
| 7,271,895 B2 | 9/2007 | Khamizov et al. |
| 7,276,158 B1 | 10/2007 | Shukla et al. |
| 7,309,409 B2 | 12/2007 | Amirkhanian et al. |
| 7,521,020 B2 | 4/2009 | Gratzl et al. |
| 7,595,026 B2 | 9/2009 | Hudson |
| 7,759,112 B2 | 7/2010 | Belgrader |
| 7,964,097 B2 * | 6/2011 | Belov et al. ............ 210/198.2 |
| 2002/0110495 A1 | 8/2002 | Hunt et al. |
| 2003/0007897 A1 | 1/2003 | Creasey |
| 2003/0068317 A1 | 4/2003 | Lee et al. |
| 2003/0173284 A1 | 9/2003 | Baker |
| 2004/0038316 A1 | 2/2004 | Kaiser et al. |
| 2004/0147042 A1 | 7/2004 | Gratzl et al. |
| 2004/0171166 A1 | 9/2004 | Hunter |
| 2004/0191537 A1 | 9/2004 | Lubda et al. |
| 2004/0224425 A1 | 11/2004 | Gjerde et al. |
| 2005/0003211 A1 | 1/2005 | Harada et al. |
| 2005/0019951 A1 | 1/2005 | Gjerde et al. |
| 2005/0139536 A1 | 6/2005 | Belov et al. |
| 2005/0178709 A1 | 8/2005 | Nakanishi et al. |
| 2005/0254995 A1 | 11/2005 | Sostek et al. |
| 2005/0281710 A1 | 12/2005 | Crabtree |
| 2006/0062701 A1 | 3/2006 | Nakamura et al. |
| 2006/0093518 A1 | 5/2006 | Shukla et al. |
| 2006/0118491 A1 | 6/2006 | Gjerde et al. |
| 2006/0201881 A1 | 9/2006 | Marcus et al. |
| 2006/0216206 A1 | 9/2006 | Hudson et al. |
| 2007/0017870 A1 | 1/2007 | Belov et al. |
| 2007/0071649 A1 | 3/2007 | Marcus |
| 2007/0075007 A1 | 4/2007 | Belov et al. |
| 2007/0111194 A1 | 5/2007 | Pellaux et al. |
| 2007/0116607 A1 | 5/2007 | Wang et al. |
| 2007/0215543 A1 | 9/2007 | Haidle |
| 2011/0210057 A1 | 9/2011 | Belov et al. |

FOREIGN PATENT DOCUMENTS

| | | |
|---|---|---|
| EP | 0729028 | 8/1996 |
| EP | 02926492 | 6/1999 |
| JP | 61-265567 | 11/1986 |
| JP | 06-315603 | 11/1994 |
| JP | 08-027621 | 12/1996 |
| JP | 11-230956 | 8/1999 |
| JP | 11295282 | 10/1999 |
| JP | 11-349692 | 12/1999 |
| JP | 2000-515066 | 11/2000 |
| JP | 2000-342982 | 12/2000 |
| JP | 2001-074756 | 3/2001 |
| JP | 2002-519643 | 7/2002 |
| JP | 2002-544486 | 12/2002 |
| JP | 2003-251122 | 9/2003 |
| JP | 2004-160368 | 6/2004 |
| JP | 2004-517310 | 6/2004 |
| JP | 2004-237142 | 8/2004 |
| JP | 2005-529335 | 9/2005 |
| JP | 2006-509994 | 3/2006 |
| JP | 3759910 | 3/2006 |
| JP | 2007-255912 | 10/2007 |
| JP | 2008-022735 | 2/2008 |
| JP | 62-004440 | 1/2010 |
| RU | 2060498 | 5/1996 |
| RU | 2114427 | 6/1998 |
| RU | 2190846 | 10/2002 |
| SU | 2114427 | 6/1998 |
| WO | WO 99/067647 | 12/1999 |
| WO | WO 00/68689 | 11/2000 |
| WO | WO 01/007162 | 2/2001 |
| WO | WO 02/40131 | 5/2002 |
| WO | WO 02/053256 | 7/2002 |
| WO | WO 02/060115 | 8/2002 |
| WO | WO 02/063300 | 8/2002 |
| WO | WO 03/104814 | 12/2003 |
| WO | WO 2005/032688 | 4/2005 |
| WO | WO 2006/062235 | 6/2006 |
| WO | WO 2006/062236 | 6/2006 |
| WO | WO 2006/093865 | 9/2006 |
| WO | WO 2007/029616 | 3/2007 |

(56) References Cited

FOREIGN PATENT DOCUMENTS

| WO | WO 2008/036091 | 3/2008 |
|---|---|---|
| WO | WO 2009/121032 | 10/2009 |
| WO | WO 2009/121034 | 10/2009 |

OTHER PUBLICATIONS

International Preliminary Report on Patentability mailed on: Apr. 3, 2006 in International Application No. PCT/US2004/32958 filed on Sep. 30, 2004 and published as: WO 05/032688 on: Apr. 14, 2005.
International Preliminary Report on Patentability mailed on: Apr. 5, 2007 in International Application No. PCT/US2006/36719 filed on Sep. 30, 2004 and published as: WO 08/036091 on: Mar. 27, 2008.
International Preliminary Report on Patentability mailed on: Mar. 29, 2009 in International Application No. PCT/US2006/36719 filed on Sep. 30, 2004 and published as: WO 08/036091 on: Mar. 27, 2008.
International Search Report and Written Opinion mailed on: Dec. 8, 2004 in International Application No. PCT/US2004/32958 filed on Sep. 30, 2004 and published as: WO 05/032688 on: Apr. 14, 2005.
Li et al., "Factors influencing polybutadiene deposition within porous chromatographic zirconia," Journal of Chromatography A, 1997, pp. 45-52.
Lobinski et al., "Multicapilary column gas chromatography with element-selective detection", Trac, Trends in Analytical Chemistry, vol. 18, No. 7, pp. 449-460, Jul. 1, 1999.
Multicapilarry columns BeeChrom, Product Catalog for GC, ChemSpace, 2002.
Pereiro et al., "Characterization of multicapillary gas chromatography—microwave-induced plasma atomic emission spectrometry for the expeditious analysis for organometallic compounds," Journal of Chromatograpyy A, vol. 795, Issue 2, Feb. 6, 1998, pp. 359-370.
Sidelnikov et al. "Sol-gel multicapilary columns for gas-solid chromatography", Journal of Chromatography, vol. 1101, No. 1-2, pp. 325-318, Jan. 6, 2006.
Sidelnikov et al., "Polycapilary Chromatography," J. Rus. Chem. Soc., 47, 23-34, 2003.
Supplemental European Search Report mailed on: Mar. 23, 2001 in Application No. EP 068039412 filed Sep. 20, 2006.
Zhdanov, "Dependency of the efficiency of the multicapillary column on the liquid phase loading method," J. Chromatogr A., Sept 12, 2001 928(2), pp. 201-207.
Belov, Yuri P., ChromBA Inc., and Ramachandran, S., "BioTip Pipette Tips for Sample Preparation," Abstract submitted to the Eastern Analytical Symposium for publication at the Eastern Analytical Symposium, Somerset New Jersey Nov. 14, 2005-Nov. 17, 2005. As communicated by Yuri p. Belov on Jan. 30, 2011.
Belov, Yuri P., ChromBA Inc., and Ramachandran, S., "BioTip Pipette Tips for Sample Preparation," Final Program and table of contents for the Eastern Analytical Symposium, Somerset New Jersey Nov. 14, 2005-Nov. 17, 2005.
Mayr et al., "Hydrophobic, Pellicular, Monolithic Capillary Columns Based on Cross-Linked Polynorbornene for Biopolymer Separations," Anal Chem, 74, pp. 6080-6087, Dec. 1, 2002.
Gilar M. et al., "Purification of crude DNA oligonucleotides by solid-phase extraction and reversed-phase high-performance liquid chromatography," Journal of Chromatography A, 890, pp. 167-177, Aug. 18, 2000.
Gilar M. et al., "Ion-pair reversed-phase high-performance liquid chromatography analysis of oligonucleotides: Retention prediction," Journal of Chromatography A, 958, pp. 167-182, Jun. 7, 2002.
International reliminary Report on Patentability mailed on: Oct. 7, 2010 in International Application No. PCT/US2009/038688 filed on Mar. 27, 2009 and published as: WO on: Oct. 15, 2009.
International Search Report and Written Opinion mailed on: Nov. 17 2009 in International Application No. PCT/US2009/038688 filed on Mar. 27, 2009 and published as: WO on: Oct. 15, 2009.
International Preliminary Report on Patentability, mailed on: Sep. 28, 2010 in International Application No. PCT/US2009/038686 filed on Mar. 27, 2009 and published as: WO 09/121032 on: Oct. 1, 2009.
International Search Report and Written Opinion, mailed on: Feb. 3, 2010 in International Application No. PCT/US2009/038686 filed on Mar. 27, 2009 and published as: WO 09/121032 on: Oct. 1, 2009.
Office Action mailed May 17, 2012 in U.S. Appl. No: 13/105,833, filed May 11, 2011.
European Search Report dated: Apr. 20, 2012 in European Patent Application No. EP09723731 filed on Mar. 27, 2009.
Hallmark et al., "Hollow Microcapillary Arrays in Thin Plastic Films," Advanced Engineering Materials, vol. 7, No. 6, Jun. 1, 2005 pp. 545-547.
Office Action mailed on Jul. 31, 2013 in U.S. Appl. No. 12/934,967, filed on Jan. 21, 2011 and published as US 2011-0107855 on May 12, 2011.
Office Action mailed on Sep. 11, 2013 in U.S. Appl. No. 12/934,974, filed on Dec. 22, 2010 and published as US 2011-0092686 on Apr. 21, 2011.
Office Action dated: Jan. 11, 2013 in U.S. Appl. No. 12/934,974, filed on: Dec. 22, 2010 and published as: 2011/0092686 on Apr. 21, 2011.
Office Action mailed Dec. 27, 2012 in U.S. Appl. No: 13/105,833, filed May 11, 2011.
European Search Report dated: Mar. 19, 2013 in European Patent Application No. EP 12173003 filed on Sep. 20, 2006.

\* cited by examiner

Gel Comparing Sample Capacity and Recovery of Multicapillary Sample Preparation Device vs. Conventional Device Gel Comparing Sample Reproducibility of Multicapillary Sample Preparation Device vs. Conventional Device

MULTICAPILLARY DEVICE FOR SAMPLE PREPARATION

REFERENCE TO RELATED APPLICATIONS

This application is a continuation of U.S. patent application Ser. No. 11/524,426, filed Sep. 20, 2006, which is a continuation-in-part of U.S. patent application Ser. No. 10/955,377 filed Sep. 30, 2004 (issued as U.S. Pat. No. 7,166,212), which claims the benefit of U.S. Provisional Patent Application No. 60/507,474 filed Sep. 30, 2003. The entirety of each of these patent applications is incorporated by reference herein, including all text and drawings.

BACKGROUND OF THE INVENTION

1. Field of the Invention

The present invention relates to a multicapillary sample preparation device especially useful for handling biological samples. In particular, the multicapillary device is suitable for use with a pipette, micropipette, syringe, or other similar analytical instrument.

2. Background Art

Many biological samples are commonly separated by gel electrophoresis and analyzed by matrix assisted laser desorption/ionization mass spectrometry (MALDI-MS). One disadvantage of these techniques, however, is that analysis is strongly affected by the presence of salts, buffers and low molecular weight organic compounds commonly used in the preparation of biological samples. In order to improve the sensitivity and selectivity of analyses, adsorptive and membranous devices are frequently used to purify and concentrate the sample prior to analysis. Such devices feature a bed of porous adsorbent or a semipermeable membrane fixed in a housing of a suitable dimension and shape that traps desired constituents, while allowing contaminants to pass.

To handle samples in the 0.01 to 100 microgram (µg) range, pipettes, micropipettes, syringes or similar analytical instruments (collectively referred to hereinafter as "pipettes") are commonly employed. The tip of these pipettes is fitted with one or more adsorptive or membranous plugs capable of purifying, concentrating, or fractionating peptides and other biomolecules.

A principal shortcoming of adsorptive and membranous plugs, however, is that porous materials are generally not effective at separating smaller biomolecules such as proteins and polynucleotides. Porous plugs are also deficient with respect to isolating and purifying larger biological materials and nucleic acids such as DNA, RNA and cells. This shortcoming derives from the fact that during sample processing, molecules must wend through a labyrinth of sponge-like, expansive and porous adsorbent silica.

There is little uniformity, consistency, and reproducibility of porous materials used for sample preparation. Sample loss in existing pipette tips is typically about 40-60%. Poor sample recovery is largely due to the fact that a sample must travel through irregular voids in the porous material, whereby a portion of the sample lodges in small voids and is unrecoverable. Moreover, in order to achieve adequate results, samples must be passed through porous materials multiple times (e.g., ten). The sample preparation devices are usually not reusable and fit poorly with automatic instrumentation because poor sample recovery may give rise to contamination due to sample carry-over.

Spin columns and other apparatus operated by a centrifuge rotor are commonly used for the isolation and purification of biological and nucleic acid samples. However, it is desirable in certain applications to avoid the use of a centrifuge for rotating a specimen to be isolated and purified. This is due, in part, to the fact that horizontal separation may result in centrifugal forces of up to, for example, 4,000 RPM, being exerted on or transmitted along the vertical axis of the spin column and sample in order to achieve satisfactory separation. Air resistance negatively affects the spin column by generating drag and friction, which heat the spin column and its contents. Considerable breakage of sample fragments is unavoidable due to the heat transfer, acute centrifugal force and accompanying air resistance. The impaired quality of biological and nucleic acid samples extracted during spin column and centrifugal processing is highly undesirable to the user.

It can be seen, therefore, that the purification and concentration of biological and nucleic acid samples using porous materials prior to instrumental analysis is time consuming, is poorly reproducible, has low throughput, and requires repeated passing of a sample through the porous plug.

Accordingly, it is an object of the present invention to provide an efficient sample preparation device for use in isolating (immunoassay), purifying and concentrating samples of proteins, peptides, nucleic acids (e.g., DNA and RNA), and other biological materials (e.g., cells) prior to analysis.

It is also an object of the invention to provide a sample preparation device with high sample capacity that increases throughput and reduces sample loss.

It is a further object of the invention to provide a highly reproducible sample preparation device that achieves uniformity, consistency, and nearly identical pathways for sample passage.

It is a still further object of the invention to provide a sample preparation device that is simple, cost-effective, and does not require the use of a silica type porous substrate or special equipment such as a centrifuge.

SUMMARY OF THE INVENTION

The invention is a high surface area multicapillary sample preparation device especially useful for handling biological samples. The multicapillary device does not require use of a silica type porous substrate. Rather, the device incorporates a plurality of parallel capillary tubes, wherein the cavity of each tube remains open and unobstructed throughout sample processing. The capillary tubes of the device function independently of one another so that sample molecules are incapable of being physically exchanged or diffusing from one capillary to another. The multicapillary device is preferably disposed in a housing that is suitable for attachment to a "pipette" or other sample preparation or analytical instrument, enabling the isolation, purification, concentration and/or fractionation of nucleic acids or biological samples in the micro- and nano-liter range, as well as larger mass loads and volumes. In an embodiment of the invention, the multicapillary device features a monolithic element pierced with multiple uniform capillaries. The monolithic element is typically mounted in the lower end of a pipette tip, syringe needle or tubing, and is operated using a pipette.

For protein separation and purification applications, an insoluble stationary phase material is deposited onto the interior surfaces (walls) of each capillary tube, without employing a supporting or intermediary constituent.

The invention also includes a method of preparing a multicapillary device for protein sample preparation. In such method, inner walls of the capillary tubes are first coated with a stationary phase material, and then the monolithic element is mounted in an appropriate housing. Alternatively, the monolithic element can first be fixed in a housing, after which the capillary walls can be coated with the stationary phase. For operation, the multicapillary sample preparation device is attached to a pipette, micropipette, tube, syringe or similar analytical instrument.

DETAILED DESCRIPTION OF THE INVENTION

In accordance with the present invention, a parallel capillary array or multicapillary sample preparation device 12 is provided for use with commercially available pipettes to permit the isolation, purification, concentration and/or fractionation of biological samples in the micro- and nanoliter range, as well as larger mass loads and volumes. The invention includes both detachable and integrally embedded multicapillary devices 12 adapted for use with manual and automatic pipettes, micropipettes 20, syringes 22 and other sample handling or analytical instruments. Notably, the multicapillary device 12 does not require use of a silica type porous substrate.

Figure 1:
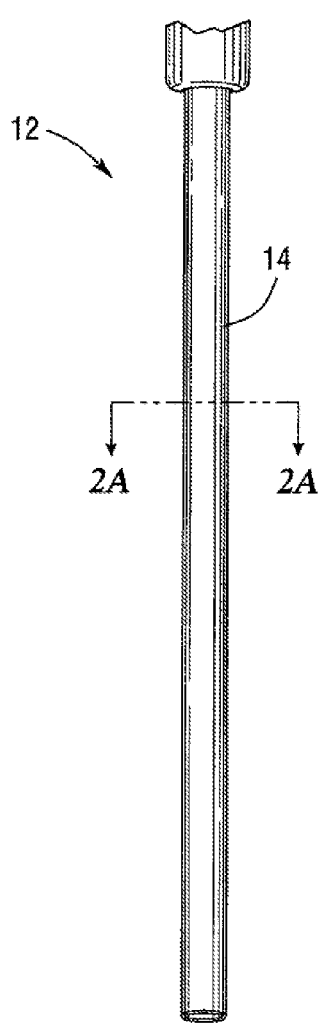
FIG. 1 is a perspective view of a multicapillary device for sample preparation in accordance with an embodiment of the present invention. Individual capillaries of the device are shown in the enlarged, cross-sectional views of FIGS. 2A, 2C and 2D (SEM).

Referring now to FIGS. 1 and 2, there is shown a multicapillary device for sample preparation 12 comprising a monolithic element (rod, tube, etc.) 14 that has an upper end and a lower end, and defines a chamber. Capillary tubes 16 of uniform internal diameter and length are arranged within the chamber. Each capillary tube 16 includes a non-porous or imperforate wall having an inner and an outer surface, which defines an inner bore. Each tube 16 also includes a first and a second opening at opposing ends, so that resistance and backpressure are low.

For protein or peptide separation and purification applications, it is preferable to deposit an insoluble stationary phase 18 on imperforate inner walls of the capillary tubes 16. For the separation and purification of polar compounds such as nucleic acids (e.g., DNA and RNA), it is preferable that the insoluble stationary phase 18 comprise a polar material. In a preferred embodiment of the invention, the thickness of the stationary phase 18 is correlated with the radius of individual capillary tubes 16 to optimize efficiency of the multicapillary device 12. As a result, during application of the stationary phase 18, a greater amount settles on the inner surface of wider capillaries; while a smaller amount settles on the inner surface of narrower capillaries. Through this process, the capillaries 16 achieve quasi-uniformity, which substantially increases the efficiency of the multicapillary device 12. The following relationship for high peak efficiency has been derived by the inventors:

$$d_f(r) = c_f r^n \qquad \text{(Equation 1)}$$

The stationary phase film thickness $d_f$ is proportional to capillary radius r in power n, where n>1; $c_f$ is a constant.

In a more preferred embodiment, the thickness of the stationary phase coating 18 is proportional to the radius of the capillary tubes 16 in power n, where n is greater than 1.

To achieve the highest peak efficiency, the stationary phase thickness $d_f$ is proportional to capillary radius r in power 3.

Stationary phase media 18 is retained on the interior surfaces of the imperforate, hollow capillary tubes 16 via stable chemical bonding or cross-linking. There is, therefore, no discharge of stationary phase media 18 into the mobile phase during separation, reducing sample contamination. In the open tubular system of the multicapillary device 12, supporting intermediary constituents and adsorptive and membranous plugs (e.g., porous adsorbent silica particles or fibers) are unnecessary. The lumen or inner cavity of each capillary tube 16 remains unobstructed and impediment free throughout the protein, peptide, nucleic acid or biological sample separation process. In this stable, surface-mediated mechanism of separation, sample molecules are incapable of diffusing between and through the imperforate walls of the capillary tubes 16 or from one capillary to another. Individual capillary tubes 16 remain physically and functionally independent of one another.

The multicapillary device for sample preparation 12 may be detachably mounted (mechanically) or fixedly inserted (e.g., by melting or adhesion) about the end portion of a pipette tip, needle, tubing or other housing of suitable shape and dimension that is attachable to a pipette 20. The multicapillary device 12 receives a sample in a mobile (liquid) phase at its first end, and a concentrated and purified sample, devoid of contaminants such as salts and buffers, is discharged at a second end of the device 12.

Figure 2A:
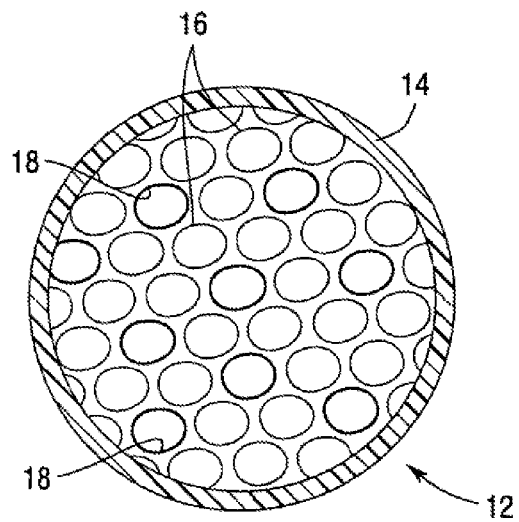
FIG. 2B is an exploded, perspective view of an individual capillary tube.
Figure 2B:
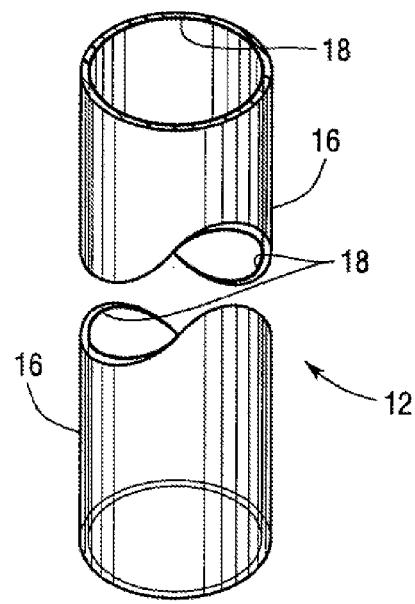
Figure 2C:
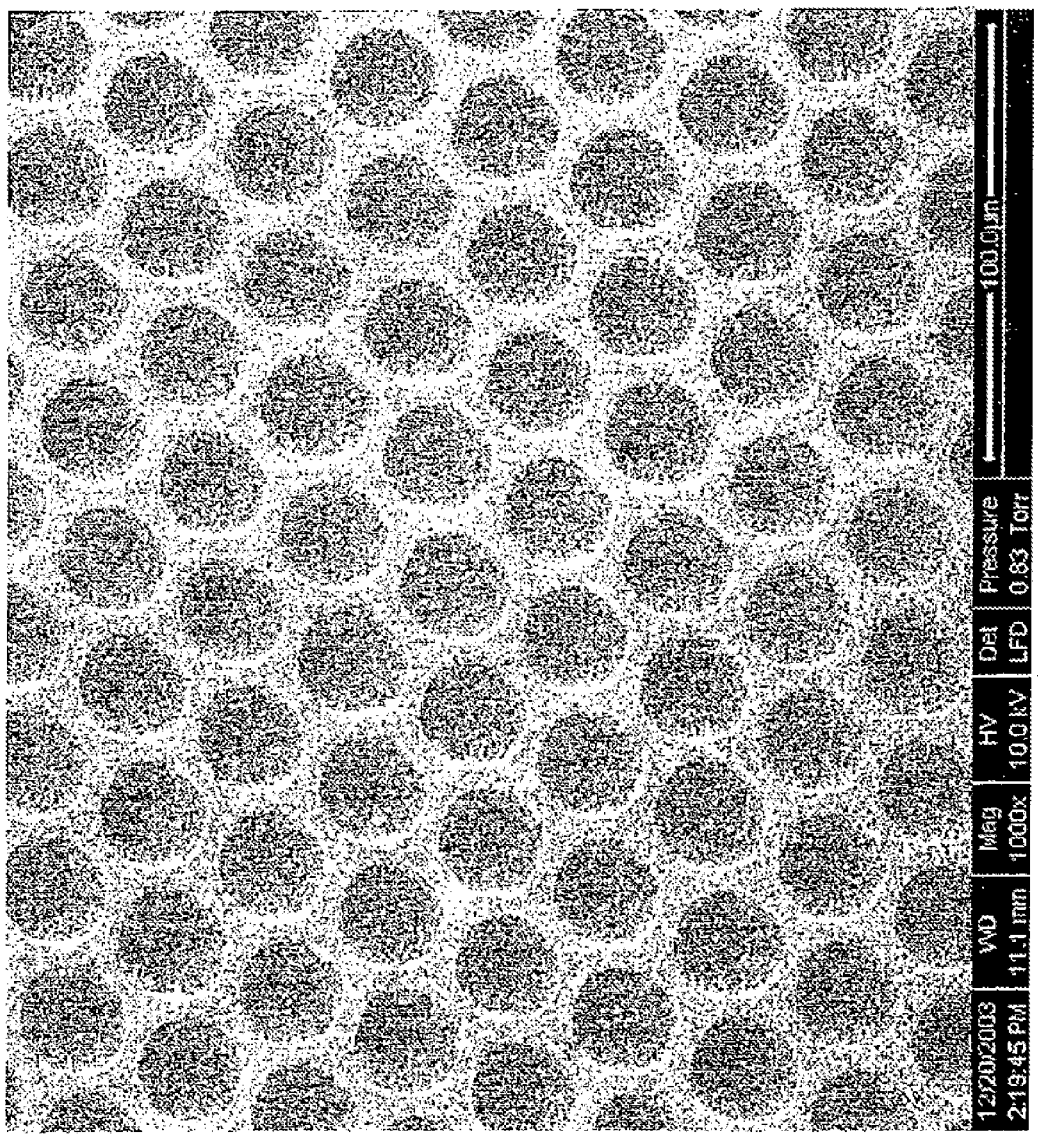
Figure 2D:
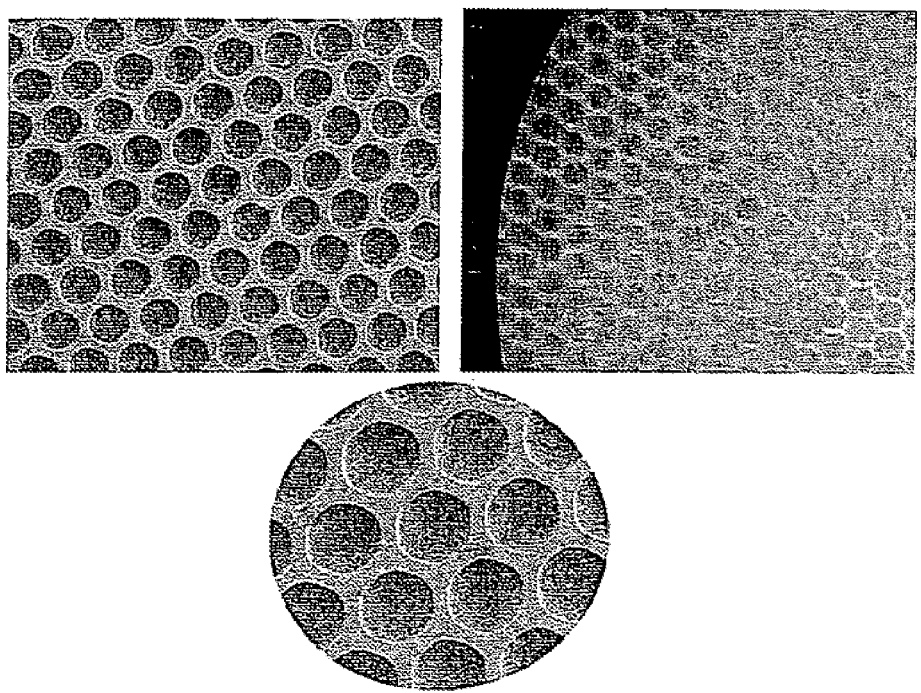
Figure 3A:
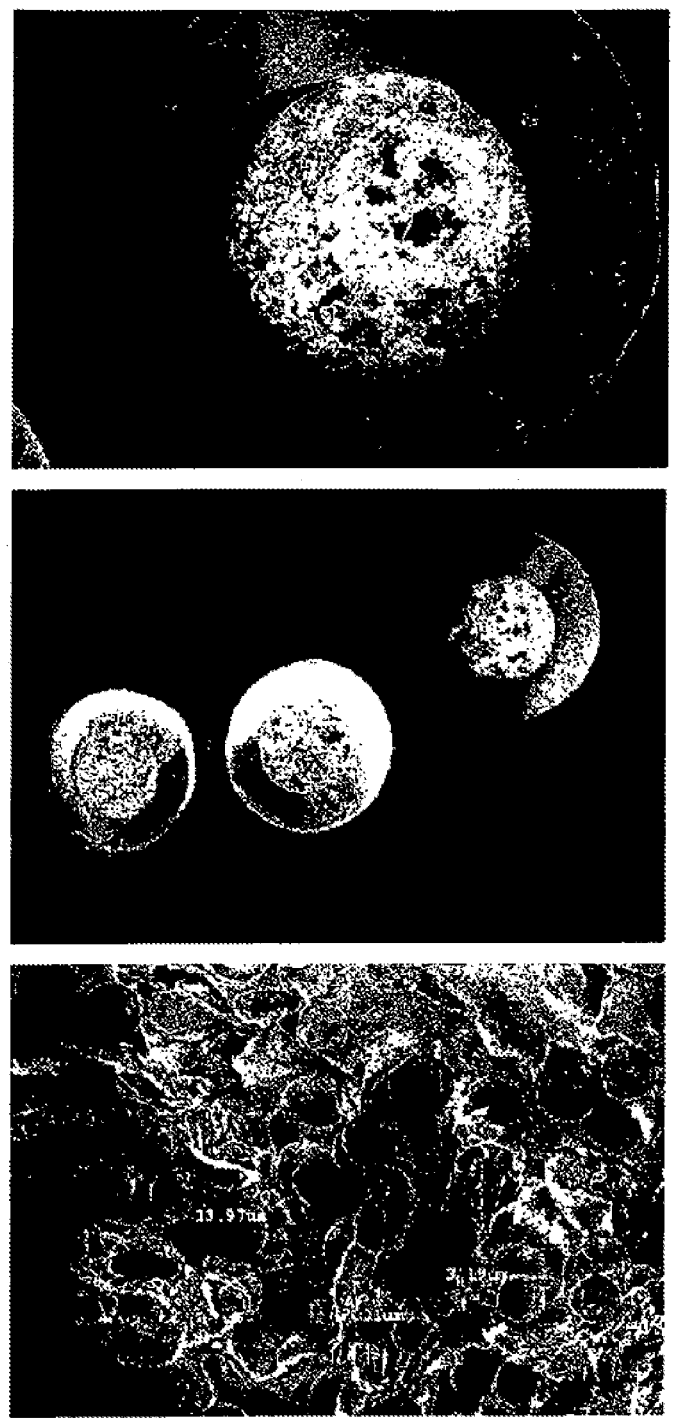
FIG. 3 depicts SEM images showing cross-sectional views of a conventional sample preparation device.
Figure 3B:
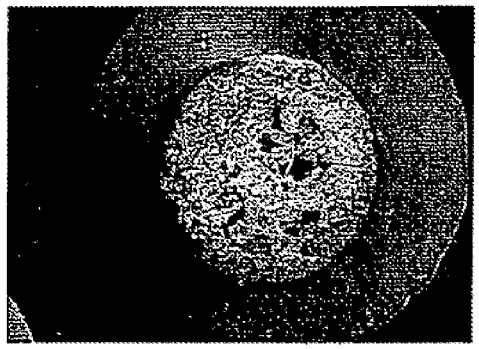
Figure 3B:
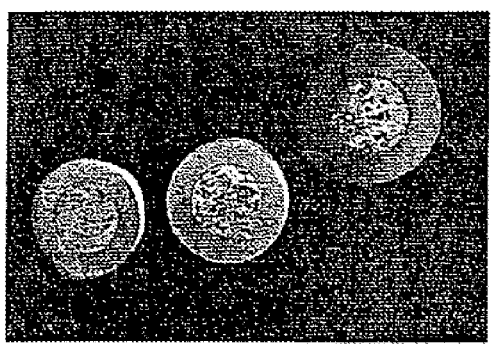
Figure 3B:
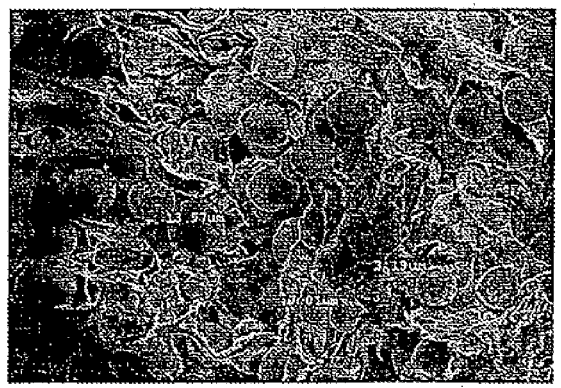

As shown in FIGS. 2A, 2B and 2C (Scanning Electron Microscope image), the structure of the multicapillary device 12 is distinctive and dissimilar to conventional spin columns and silica-based adsorptive and membranous "plugs" (see FIGS. 3 and 11), which feature irregular voids and vastly different sample pathways that entrap biological samples, such that more than half of the sample is usually unrecoverable. The multicapillary device 12 comprises a plurality of uniform capillary tubes 16 having an insoluble stationary phase media 18 on internal surfaces thereof, thereby permitting a sample inserted into the flow passage of the multicapillary device 12 to advance through open and virtually identical pathways. The inner cavity or flow passage of each capillary tube 16 thus remains unobstructed and impediment free throughout the sample separation process.

As shown in FIGS. 12 and 13, purified (DNA) sample fragments extracted from the open and unobstructed capillary channels of the multicapillary device 12 comprise considerably larger fragments, representing a significant decrease in fragment breakage or "shearing." These larger fragments generally reflect a better quality of purified sample as compared to conventional porous silica plugs used for sample processing. In the conventional adsorptive and membranous plugs, sample must travel through tortuous and irregular voids in the porous material, whereby portions of the sample lodge in small voids and are unrecoverable. Fragment shearing is thus unavoidable. With its open and unobstructed channel structure, the multicapillary device 12 of the present invention achieves substantial uniformity and consistency as compared to the sponge-like and expansive porous silica materials currently used for sample preparation.

Due to the significant reduction in sample loss enabled by the open and unobstructed channel structure of the multicapillary device 12, it is unnecessary for sample to be passed through the separation materials multiple times, as required in existing porous silica plugs, particles (for proteins and peptides), and fibers (for DNA and RNA). As a result, the multicapillary device 12 is generally reusable and fits conveniently with automatic instrumentation because there is no contamination due to sample carry-over. In short, the present multicapillary device 12 demonstrates superior characteristics over conventional adsorptive and membranous plugs with respect to binding capacity, recovery, increased throughput, uniformity and reproducibility.

In one embodiment of the invention, the imperforate inner walls of the capillary tubes 16 include particles of inert material or a nodular or uneven surface for increasing the surface area of the multicapillary device 12. In such case, the inner wall may be altered using an etching process in combination with a solvent such as, for example, a mineral acid or base, or an organic acid or base.

The present invention encompasses the use of any stationary phase 18 and surface chemistry adapted for liquid chromatography and sample preparation applications. In some embodiments, the stationary phase media 18 deposited on inner surfaces of the capillary wall comprises a monolayer of organic molecules, biopolymers or larger particles. Such molecules and particles include, but are not limited to, hydrocarbons and their C-, N-, S-, and P-derivatives; proteins, nucleic acids, and polysaccharides; linear and cross-linked polysiloxanes and other polymers; and viruses and cells. In other embodiments, a stationary phase coating 18 is formed by treating inner surfaces of the capillaries 16 with organosilicone compounds and further modifying these groups with appropriate reagents and particles.

An alternative technique for the deposition of a stationary phase 18 involves polymerization of unsaturated compounds, such as butadiene, styrene, divinylbenzene, and others, on inner walls of the capillary tubes 16.

The techniques used for deposition of a stationary phase material 18, described in the following Examples, render the stationary phase material insoluble in organic and water-organic solvents commonly used in sample preparation and liquid chromatography, such as acetonitrile, methanol, isopropanol, acetone, dimethylsulfoxide, dimethylformamide and urea; acetic, iodoacetic, trifluoroacetic and formic acids; and phosphate, acetic and carbonate buffers, etc.

Figures 4A, 4B:
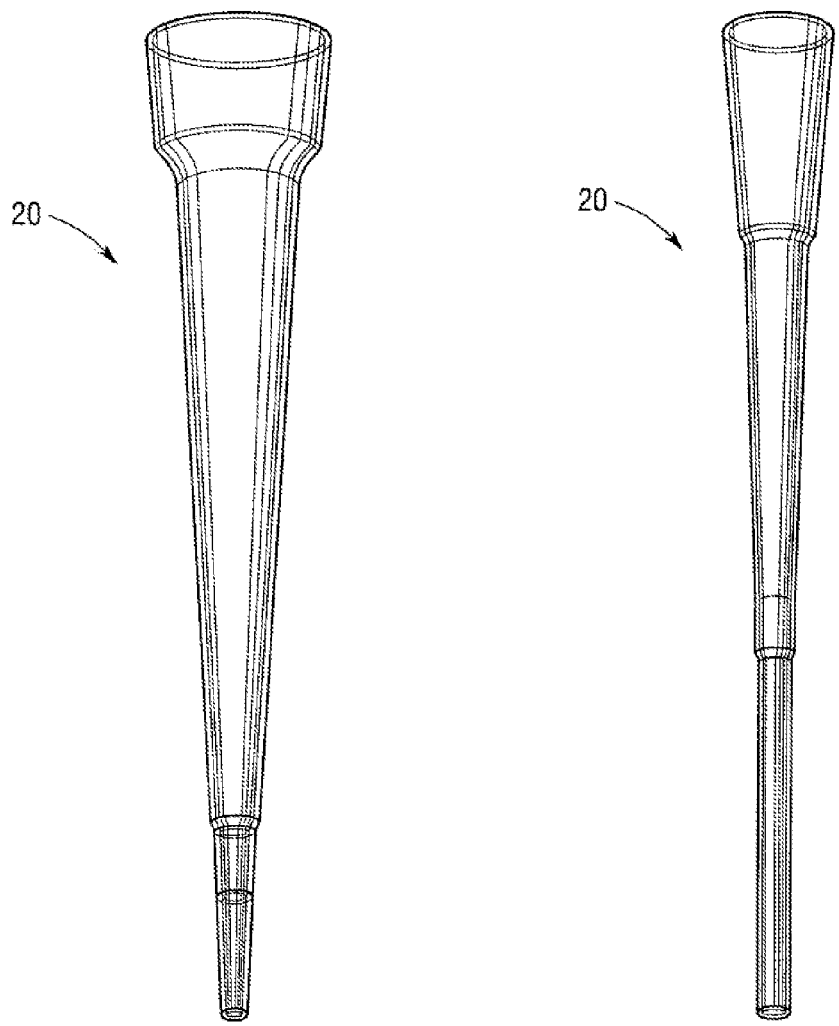
FIGS. 4A-4D are perspective views of pipette tips and a pipette format multicapillary device, respectively, in accordance with the present invention.
Figure 4C:
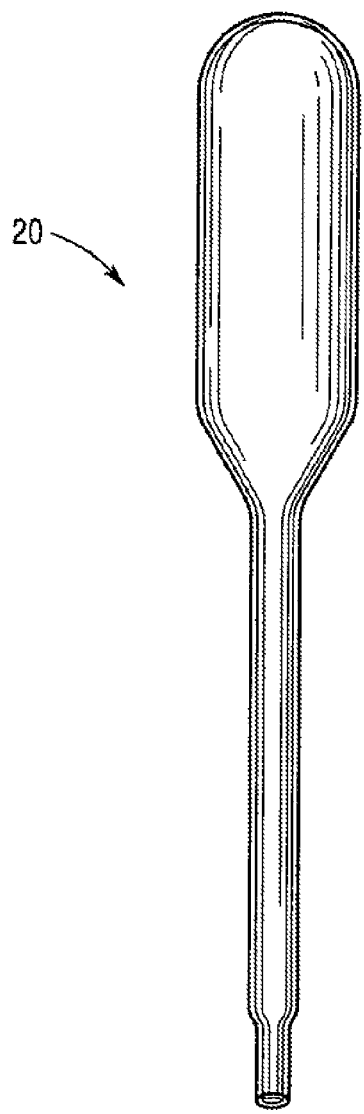
Figure 4D:
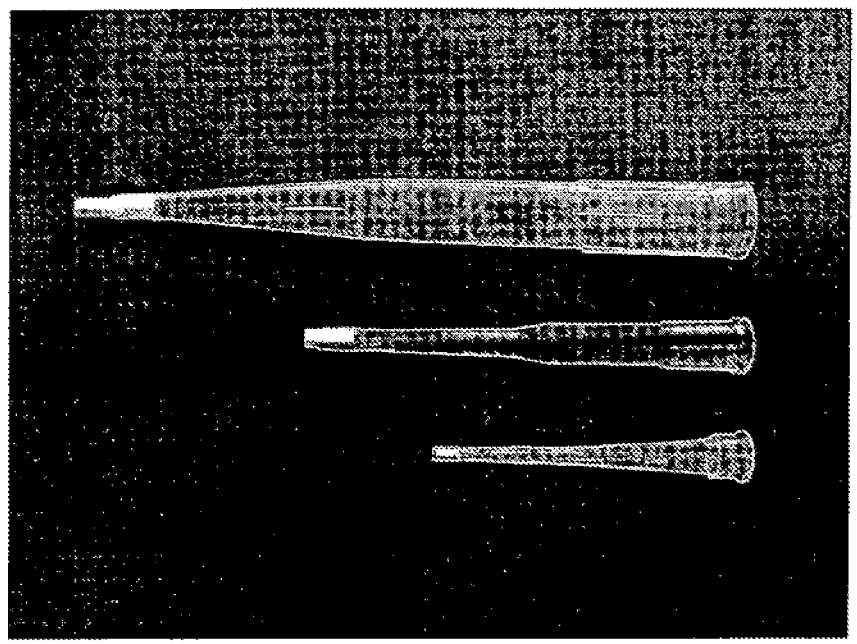
Figure 5A:
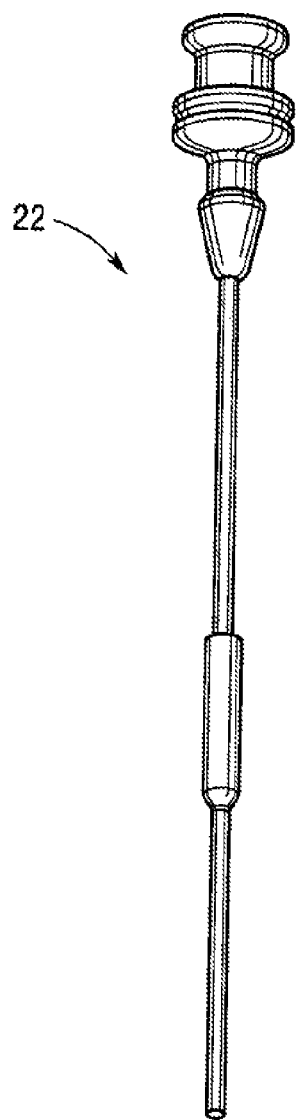
FIGS. 5A-5C show perspective views of a syringe format multicapillary device for sample preparation according to the present invention.
Figures 5B, 5C:
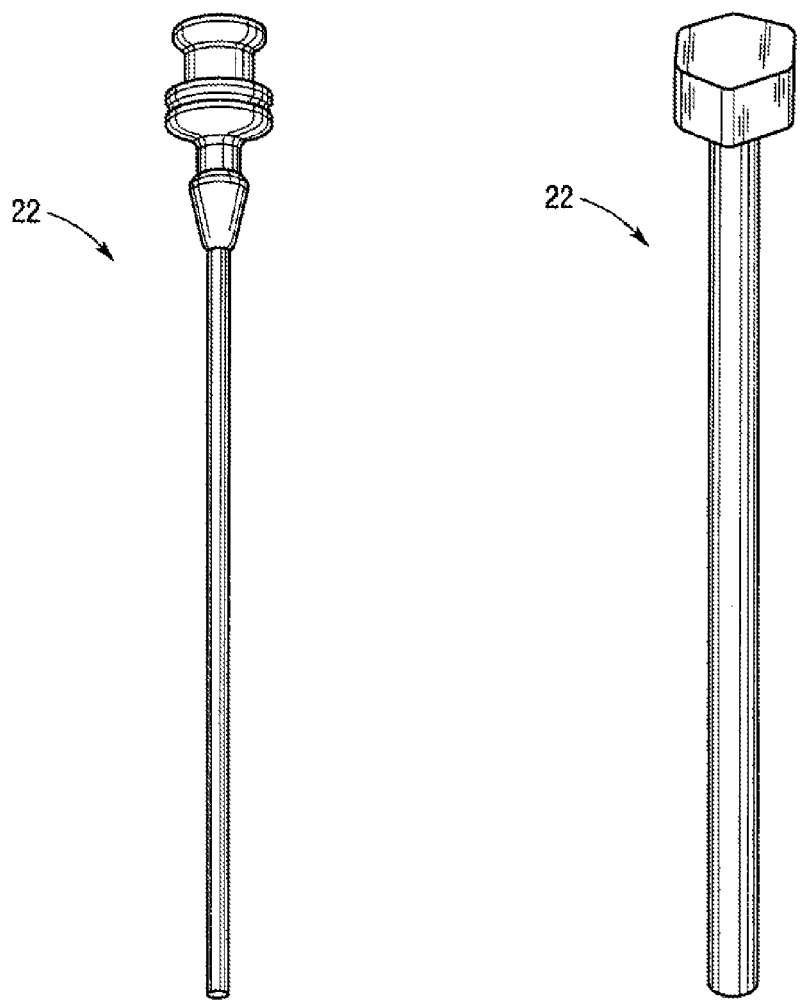
Figure 6:
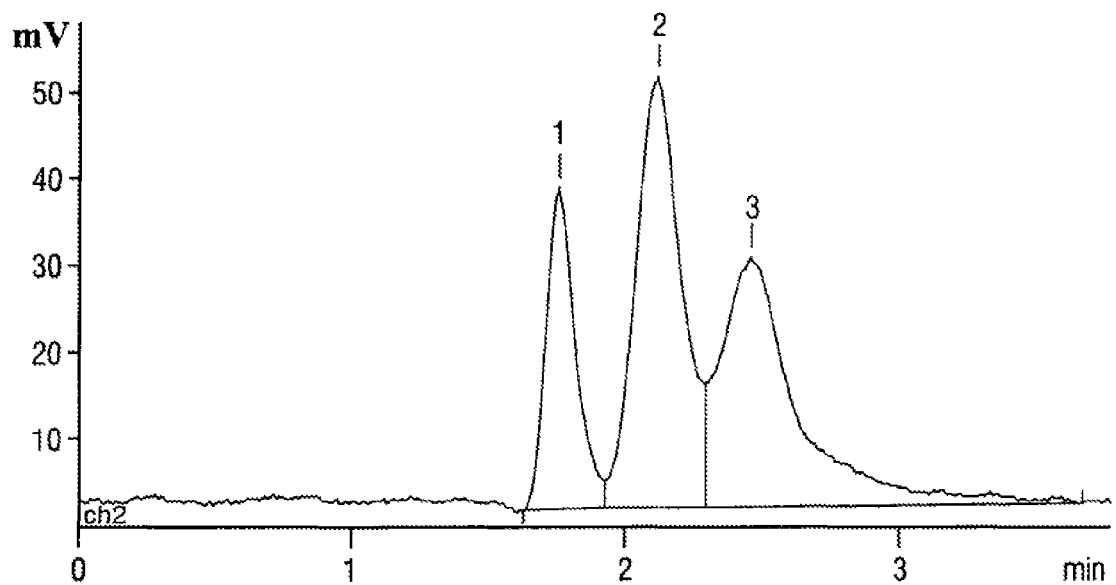
FIG. 6 is a chromatogram showing the separation of a three component mixture in a multicapillary device for sample preparation according to the present invention.
Figure 7A:
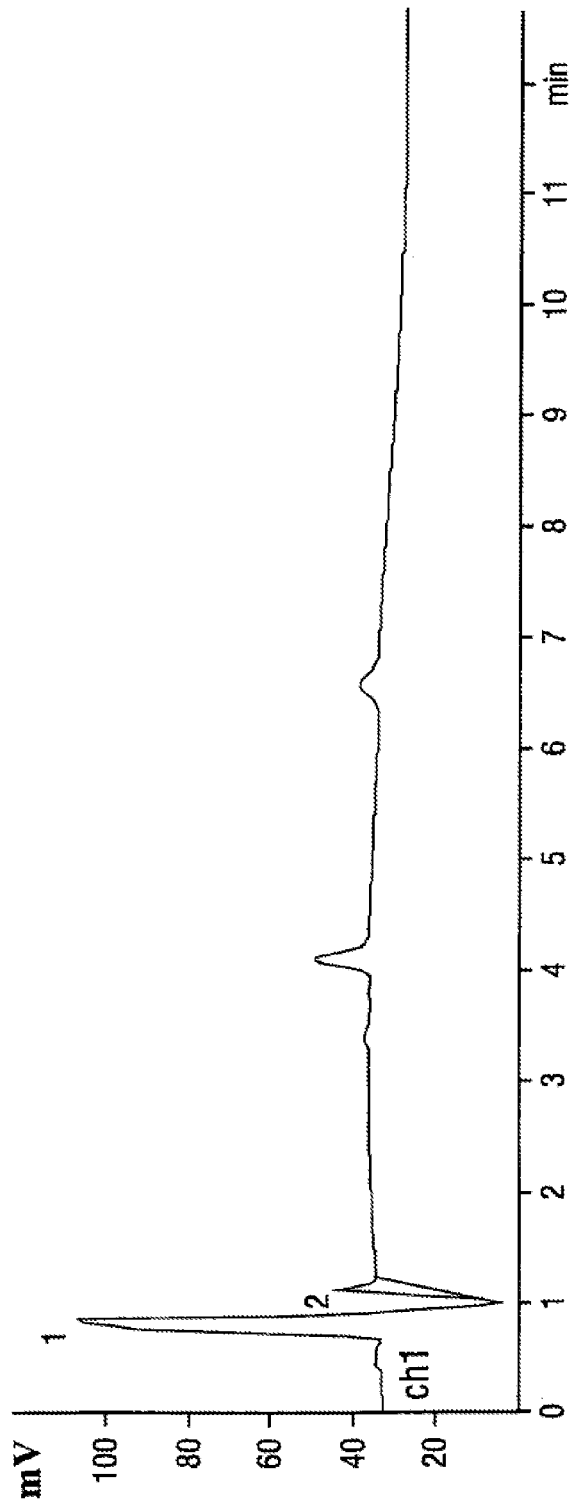
FIG. 7A is a chromatogram illustrating the performance of a multicapillary sample preparation device in sample enrichment as compared to a standard SPE cartridge, FIG. 7B.
Figure 7B:
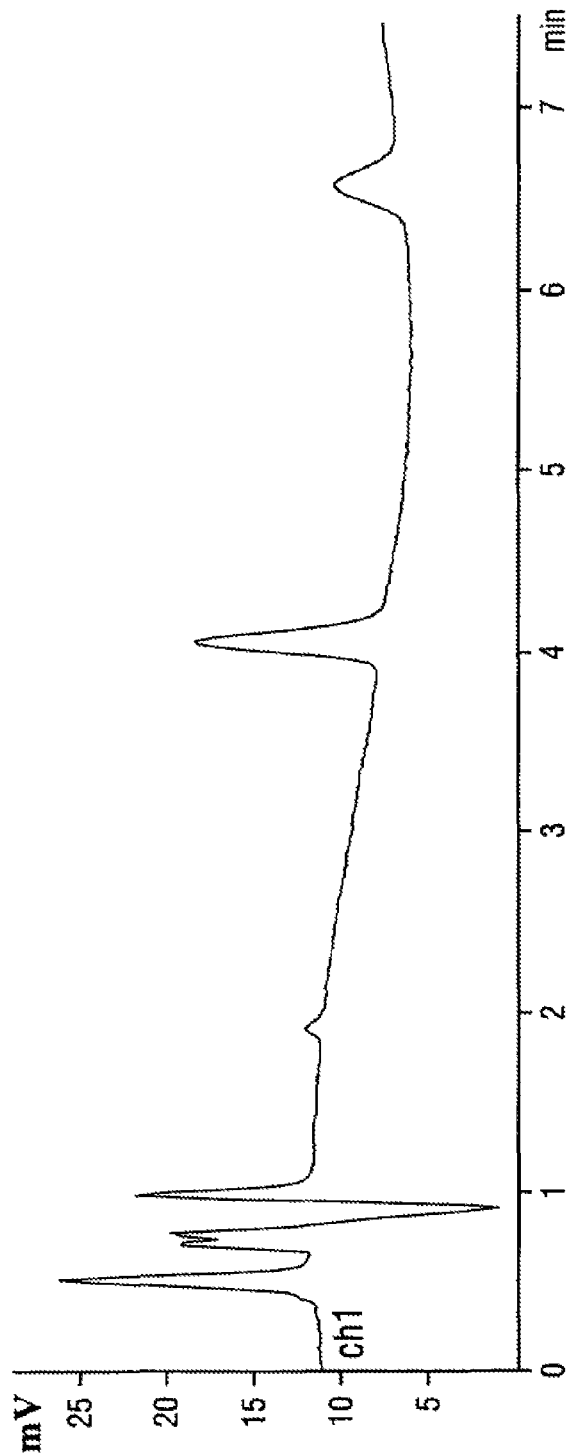

The multicapillary sample preparation device 12 is advantageously suited for use with a wide range of sample preparation and analytical instruments. As shown in FIGS. 1, 4, and 5, these include, but are not limited to, manual and automatic pipettes and micropipettes 20, syringes 22, disposable devices, and automatic sample handling instruments. In some embodiments, the multicapillary device 12 is inserted about the terminal portion of a pipette tip 20 or other appropriate housing by, for example, sliding or press fitting, and is detachably retained in place by mechanical means such as elastic sealing rings and/or walls of the housing.

In other embodiments, the multicapillary device 12 is integrally and permanently embedded (e.g., cast-in-place) about the terminal region of a pipette tip 20 or other housing by melting, heat shrinking or adhesion in order to fuse the monolithic element 14 to the surface of a pipette tip 20 or other housing commonly made from polypropylene or other thermoplastic material. As an alternative, plasma and/or chemical means may be used to accomplish adhesion of the monolithic element 14 to the surface of the pipette tip 20 or other housing.

In yet another embodiment, the multicapillary device 12 is adapted to be detachably or fixedly engaged or aligned with the hollow flow passage(s) of a substantially cylindrical, conical or other housing configuration. The multicapillary device 12 is suitably sized and shaped to be integrated in housings of varying sizes and configurations. However, it is preferable that the housing have a volume in the range of about 0.1 µL to about 100 mL, more preferably in the range of about 1 to about 1000 µL, and most preferably in the range of about 2 to about 200 µL.

It will be understood that any technique used to install the multicapillary device 12 into a pipette tip or other housing for operation with a pipette 20 should accurately direct sample in a liquid phase through the capillary tubes 16 of the monolithic element 14 without bypassing the element 14. In such adaptation, the multicapillary device 12 receives the sample at its first end, and a concentrated and/or purified sample, devoid of contaminants such as salts and buffers, is discharged at a second end. The multicapillary device 12 of the present invention is freely permeable not only to proteins, peptides, polynucleotides, and other molecules and biopolymers, but also to viruses, spores, cells (e.g., cancer and stem), and microorganisms. It will be understood, however, that sample molecules are prevented from diffusing from one capillary tube 16 to another Preferred materials for fabricating the monolithic element 14, capillary tubes 16, tips, pipettes 20, syringes 22 and other housings of the present invention include, but are not limited to, glass, fused silica, ceramic, metal (e.g., stainless steel), and plastic (e.g., polypropylene, polyethylene, polyolefin, or polyetheretherketone). In sample preparation and chromatographic applications, it is desirable to employ a large number (e.g. hundreds or thousands) of capillary tubes to provide an abundant surface area for higher sample loading capacity. It will be understood, however, that the number and dimensions of the multicapillary device 12, stationary phase media 18, solvent, tips and other housings employed in the invention will vary according to application.

As an example, the number of capillary tubes 16 provided in a multicapillary device 12 may range from about 100 to about 1,000,000. The inner diameter of each capillary tube 16 may range from about 0.1 µm to about 200 µm. The outer diameter of the monolithic element 14 may range from about 0.1 mm to about 1 m, and the length may range from about 0.1 mm to about 2 m. In a preferred embodiment, the number of capillary tubes 16 ranges from about 1000 to about 10,000, the inner diameter of each capillary ranges from about 5 µm to about 100 µm, the outer diameter of the monolithic element 14 ranges from about 1 mm to about 20 mm, and the length ranges from about 1 mm to about 250 mm.

EXAMPLES

Example 1

C-1 Stationary Phase

A 5% solution of trimethylchlorosilane in toluene is pumped at 10 µL/min for six hours through a 1 mm outer diameter×250 mm long multicapillary glass rod pierced with approximately 4400 capillaries of 10 µm diameter at 105° C. The multicapillary rod is rinsed with toluene, acetone and methanol, and dried with a nitrogen stream.

Example 2

C-4 Stationary Phase

A 10% solution of butyldimethylchlorosilane in toluene is pumped at 40 µL/min for six hours through a 2 mm outer diameter×300 mm long multicapillary glass rod pierced with approximately 4600 capillaries of 25 µm diameter at 105° C. The multicapillary rod is rinsed with toluene, acetone and methanol, and dried with a nitrogen stream.

Example 3

C-8 Stationary Phase

A 10% solution of octyltrichlorosilane in toluene is pumped at 50 µL/min for six hours through a 2.3 mm outer diameter×250 mm long multicapillary glass rod pierced with approximately 1400 capillaries of 40 µm diameter at 105° C. The multicapillary rod is rinsed with toluene, acetone and methanol, and dried with a nitrogen stream.

Example 4

C-12 Stationary Phase

A 5% solution of dodecyltrichlorosilane in toluene is pumped at 75 µL/min for six hours through a 6 mm outer diameter×300 mm long multicapillary glass rod pierced with approximately 3300 capillaries of 65 µm diameter at 105° C. The multicapillary rod is rinsed with toluene, acetone and methanol, and dried with a nitrogen stream.

Example 5

C-18 Stationary Phase 1

A 10% solution of octadecyltriethoxysilane in toluene is pumped at 10 µL/min for six hours through a clean and dry 2.3 mm outer diameter×300 mm multicapillary glass rod pierced with approximately 4,000 capillaries of 20 µm diameter at 105° C. While pumping the solution, an opposite end of the multicapillary device is moved at a linear speed of 0.5 mm/min inside an oven heated to 150° C. The device is rinsed with toluene, acetone and methanol, and dried with a nitrogen stream.

Example 6

C-18 Stationary Phase 2

Twenty 1 mm outer diameter×2.5 mm long multicapillary glass rods pierced with approximately 4400 capillaries of 10 µm diameter are placed in a flask containing 50 mL of a 5% solution of octadecyldimethylchlorosilane in toluene and equipped with a reflux condenser and a calcium chloride tube. The mixture is slowly refluxed for six hours. The liquid phase is separated and the multicapillary rods are repeatedly washed with toluene, tetrahydrofuran and methanol, and dried at room temperature.

Example 7

C-16, C-30, Phenyl, Naphthyl, and Cyano Stationary Phases

In accordance with the conditions described in Example 6, the stationary phases with C-16, C-30, phenyl, naphthyl and cyano groups are prepared, correspondingly, from hexadecyltrichlorosilane, triacontyltrichlorosilane, phenethyltrichlorosilane, (1-naphthylmethyl)trichlorosilane and 3-cyanopropyltrichlorosilane.

Example 8

Epoxide Stationary Phase

Twenty 2.3 mm outer diameter×5 mm long multicapillary glass rods pierced with approximately 1400 capillaries of 40 µm diameter are placed in a flask containing 50 mL of a 5% solution of (3-glycidoxypropyl)trimethoxysilane in toluene and equipped with a reflux condenser. The mixture is slowly refluxed for five hours while the condenser is maintained at a temperature of 70° C. to remove the methanol formed from the reaction. The liquid phase is separated and the multicapillary rods are repeatedly washed with toluene, tetrahydrofuran and methanol, and dried at room temperature.

Example 9

Diol Stationary Phase 1

Twenty 2.3 mm outer diameter×3 mm long multicapillary glass rods pierced with approximately 1400 capillaries of 40 µm diameter are placed in a flask containing 50 mL of a 5% solution of (3-glycidoxypropyl)trimethoxysilane in toluene and equipped with a reflux condenser. The mixture is slowly refluxed for three hours while the condenser is maintained at a temperature of 70° C. The liquid phase is separated and the multicapillary rods are repeatedly washed with toluene, tetrahydrofuran, methanol and water. 50 mL of water is added and the pH is adjusted to 2.0 with nitric acid. The mixture is slowly agitated for two hours at room temperature. The liquid phase is separated and the multicapillary rods are washed with water until the wash is neutral, then washed three times with methanol, and dried at room temperature.

Example 10

Diol Stationary Phase 2

2.5 g of (3-glycidoxypropyl)trimethoxysilane is dropped into a flask containing 50 mL of water, while maintaining the pH between 5 and 6 with 0.01 M potassium hydroxide. Twenty 2.3 mm outer diameter×5 mm long multicapillary glass rods pierced with approximately 1400 capillaries of 40 µm diameter are placed in a flask. The mixture is slowly refluxed for three hours with a reflux condenser. The liquid phase is separated and the multicapillary rods are repeatedly washed with water, methanol and tetrahydrofuran. 50 mL of water is added and the pH is adjusted to 2.0 with nitric acid. The mixture is slowly agitated for two hours at room temperature. The liquid phase is separated and the multicapillary rods are washed with water until the wash is neutral, then washed three times with methanol, and dried at room temperature.

Example 11

Amino Stationary Phase

Twenty-five 1 mm outer diameter×2.5 mm long multicapillary glass rods pierced with approximately 4400 capillaries of 10 µm diameter are placed in a flask containing 50 mL of a 5% solution of 3-aminopropyltrimethoxysilane in toluene and equipped with a reflux condenser. The mixture is slowly refluxed for five hours while the condenser is maintained at a temperature of 70° C. The liquid phase is separated and the multicapillary rods are repeatedly washed with toluene, tetrahydrofuran and methanol, and dried at room temperature.

Example 12

Trimethylammonium Stationary Phase

Thirty 2.3 mm outer diameter×5 mm long multicapillary glass rods pierced with approximately 1400 capillaries of 40 µm diameter are placed in a flask containing 50 mL of a 5% solution of 3-aminopropyltrimethoxysilane in toluene and equipped with a reflux condenser. The mixture is slowly refluxed for six hours while the condenser is maintained at a temperature of 70° C. The liquid phase is separated and the multicapillary rods are repeatedly washed with toluene, tetrahydrofuran and methanol. 30 mL of a 5% solution of trimethylamine in methanol is added to the flask. The flask is equipped with a calcium chloride tube, and the mixture is slowly agitated at 0-5° C. for 48 hours. The liquid phase is separated and the multicapillary rods are repeatedly washed with methanol, water, 0.01 M HCl, water and tetrahydrofuran, and dried at room temperature.

Example 13

Carboxylic Acid Stationary Phase

Twenty 2.3 mm outer diameter×5 mm long multicapillary glass rods pierced with approximately 1400 capillaries of 40 µm diameter are placed in a flask containing 50 mL of a 5% water solution of carboxyethylsilane triol (sodium salt). The pH is adjusted to 2.0 by adding hydrochloric acid. The mixture is slowly refluxed for three hours with a reflux condenser. The liquid phase is separated and the multicapillary rods are washed with water until the wash is neutral, then washed three times with methanol, and dried at room temperature.

Example 14

Sulfonic Stationary Phase

Twenty-five 2.3 mm outer diameter×3 mm long multicapillary glass rods pierced with approximately 1400 capillaries of 40 µm diameter are placed in a flask containing 50 mL of a 5% water solution of 3-(trihydroxysilyl)-1-propanesulfonic acid. The mixture is slowly refluxed for three hours with a reflux condenser. The liquid phase is separated and the multicapillary rods are washed with water until the wash is neutral, then washed three times with methanol, and dried at room temperature.

Example 15

Phosphonic Stationary Phase

Thirty 2.3 mm outer diameter×3 mm long multicapillary glass rods pierced with approximately 1400 capillaries of 40 µm diameter are placed in a flask containing 50 mL of a 5% water solution of (3-trihydroxysilylpropyl)methylphosphonate sodium salt. The mixture is acidified to pH 2.0 with HCL and slowly refluxed for three hours with a reflux condenser. The liquid phase is separated and the multicapillary rods are washed with water until the wash is neutral, then washed three times with methanol, and dried at room temperature.

Example 16

Iminodiacetic Acid Stationary Phase

Twenty 1 mm outer diameter×2.5 mm long multicapillary glass rods pierced with approximately 4400 capillaries of 10 µm diameter are placed in a flask containing 50 mL of a 5% solution of (3-glycidoxypropyl)trimethoxysilane in toluene and equipped with a reflux condenser. The mixture is slowly refluxed for five hours while the condenser is maintained at a temperature of 70° C. The liquid phase is separated and the multicapillary rods are repeatedly washed with toluene, tetrahydrofuran, methanol and water. 20 mL of a 2 M iminodiacetic acid solution in 0.1 M sodium borate buffer, pH 8.5, is added and the mixture is slowly agitated for 24 hours at room temperature. The liquid phase is separated and the multicapillary rods are washed with water until the wash is neutral, then washed three times with methanol, and dried at room temperature.

Example 17

Cystein Stationary Phase

Twenty-five 1 mm outer diameter×2.5 mm long multicapillary glass rods pierced with approximately 4400 capillaries of 10 µm diameter are placed in a flask containing 50 mL of a 5% solution of 3-bromopropyltrimethoxysilane in toluene and equipped with a reflux condenser. The mixture is slowly refluxed for five hours while the condenser is maintained at a temperature of 70° C. The liquid phase is separated and the multicapillary rods are repeatedly washed with toluene, tetrahydrofuran and methanol. 50 mL of a 1% solution of cystein in methanol and 1 mL of triethylamine are added, and the mixture is slowly refluxed with a reflux condenser for five hours. The liquid phase is separated and the multicapillary rods are repeatedly washed with methanol, water, methanol and methylene chloride, and dried at room temperature.

Example 18

Glutathione Stationary Phase

Twenty 1 mm outer diameter×2.5 mm long multicapillary glass rods pierced with approximately 4400 capillaries of 10

μm diameter are placed in a flask containing 50 mL of a 5% solution of 11-bromoundecyltrimethoxysilane in toluene and equipped with a reflux condenser. The mixture is slowly refluxed for five hours while the condenser is maintained at a temperature of 70° C. The liquid phase is separated and the multicapillary rods are repeatedly washed with toluene, tetrahydrofuran and methanol. 50 mL of a 0.5% solution of glutathione in methanol and 1 mL of triethylamine are added, and the mixture is slowly refluxed with a reflux condenser for five hours. The liquid phase is separated and the multicapillary rods are repeatedly washed with methanol, water, methanol and methylene chloride, and dried at room temperature.

Example 19

Chiral Stationary Phase

A 5% solution of (R)-N-1-phenylethyl-N'-triethoxysilylpropylurea in toluene is pumped at 10 μL/min for six hours through a 1 mm outer diameter×300 mm long multicapillary glass rod pierced with approximately 4000 capillaries of 10 μm diameter at 105° C. The multicapillary rod is rinsed with toluene, tetrahydrofuran and methanol, and dried with a nitrogen stream.

Example 20

Polybutadiene Stationary Phase

The 10% solution of vinyltrichlorosilane in isooctane is pumped at 20 μL/min for six hours through a 1 mm outer diameter×250 mm long multicapillary glass rod pierced with approximately 4,400 capillaries of 10 μm diameter at 90° C. The multicapillary rod is rinsed with isooctane, tetrahydrofuran, methanol, toluene and isooctane. A solution of 100 mg polybutadiene (MW 3,400) and 0.5 mg dicumyl peroxide in 100 mL of isooctane is pumped at 10 μL/min for six hours through the multicapillary rod at 90° C. The multicapillary rod is rinsed with toluene, tetrahydrofuran and methanol, and dried with a nitrogen stream.

Example 21

Biotin Stationary Phase

Twenty five 1 mm outer diameter×2.5 mm long multicapillary glass rods pierced with approximately 4400 capillaries of 10 μm diameter are placed in a flask containing 50 mL of a 5% solution of 3-aminopropyltrimethoxysilane in toluene and equipped with a reflux condenser. The mixture is slowly refluxed for five hours while the condenser is maintained at a temperature of 70° C. The liquid phase is separated and the multicapillary rods are repeatedly washed with toluene, methanol and dimethylformamide. 15 mL of a saturated dimethylformamide solution of biotin, a solution of 0.3 g of 1-hydroxybenzotriazole hydrate in 10 mL of dimethylformamide, and a solution of 0.25 g of N,N'-dicyclohehylcarbodiimide in 10 mL of dimethylformamide are added, and the mixture is slowly agitated for five hours at room temperature. The liquid phase is separated and the multicapillary rods are repeatedly washed with dimethylformamide, methanol, water, methanol and methylene chloride, and dried at room temperature.

Example 22

Heparin Stationary Phase

Twenty 2.3 mm outer diameter×2.5 mm long multicapillary glass rods pierced with approximately 1400 capillaries of 40 μm diameter are placed in a flask containing 50 mL of a 5% solution of 3-aminopropyltrimethoxysilane in toluene and equipped with a reflux condenser. The mixture is slowly refluxed for five hours while the condenser is maintained at a temperature of 70° C. The liquid phase is separated and the multicapillary rods are repeatedly washed with toluene, methanol, water and 0.05 M 2-morpholinoethane sulfonic acid buffer, pH 5.6. The 10 mL solution of 0.2 g heparin (from bovine kidney), 1 g N-(3-dimethylaminopropyl)-N'-ethylcarbodiimide, and 0.5 g N-hydroxysuccinimide in 0.05 M 2-morpholinoethane sulfonic acid buffer, pH 5.6, is added. The mixture is slowly agitated for three hours at room temperature. The liquid phase is separated, and the multicapillary rods are repeatedly washed with water, phosphate buffer, pH 8, and 20% sodium chloride, and then washed with water and stored at 4° C.

Example 23

Glycoprotein Stationary Phase

Twenty 2.3 mm outer diameter×3 mm long multicapillary glass rods pierced with approximately 1400 capillaries of 40 μm diameter are placed in a flask containing 20 mL of a 5% solution of (3-glycidoxypropyl)trimethoxysilane in toluene and equipped with a reflux condenser. The mixture is slowly refluxed for five hours while the condenser is maintained at a temperature of 70° C. The liquid phase is separated and the multicapillary rods are repeatedly washed with toluene, methanol and water. The 4 mL solution of 100 mg alpha1 acid (from bovine plasma) in a 1:1 mixture of 0.4 M sodium chloride and 0.2 M borate buffer, pH 8.5, is added. The mixture is slowly agitated at room temperature for 48 hours. The liquid phase is separated. The multicapillary rods are repeatedly washed with a 1:1 mixture of 0.4 M sodium chloride and 0.2 M borate buffer, pH 8.5, then washed with water and stored at 4° C.

Example 24

Trypsin Stationary Phase

Twenty 2 mm outer diameter×5 mm long multicapillary glass rods pierced with approximately 4600 capillaries of 25 μm diameter are placed in a flask containing 20 mL of a 5% solution of (3-glycidoxypropyl)trimethoxysilane in toluene and equipped with a reflux condenser. The mixture is slowly refluxed for five hours while the condenser is maintained at a temperature of 70° C. The liquid phase is separated and the multicapillary rods are repeatedly washed with toluene, methanol and water. A 7 mL solution of 100 mg trypsin (from bovine pancreas) in 0.2 M phosphate buffer, pH 7.0, is added to the flask. The mixture is slowly agitated at room temperature for 15 hours, and the liquid phase is separated. The multicapillary rods are repeatedly washed with 0.2 M phosphate buffer, pH 7.0, water, 0.2 M Tris buffer, pH 7.5, for two hours, and then washed with water and stored at 4° C.

Example 25

Avidin, Lectin, and Protein A Stationary Phases

In accordance with the conditions described in Example 24, avidin, lectin and protein A stationary phases are prepared using avidin (from egg white), lectin (from *Agaricus bisporus*), and protein A (from *Staphylococcus aureus*), correspondingly.

Example 26

Antibody Stationary Phase

Twenty 2.3 mm outer diameter×3 mm long multicapillary glass rods pierced with approximately 1400 capillaries of 40 μm diameter are placed in a flask containing 50 mL of a 5% solution of 10-(carbomethoxy)decyldimethylmethoxysilane in toluene and equipped with a reflux condenser. The mixture is slowly refluxed for three hours while the condenser is maintained at a temperature of 70° C. The liquid phase is separated, and the multicapillary rods are repeatedly washed with toluene, methanol and methylene chloride. A 35 mL solution of 1 mL trimethyliodosilane in methylene chloride is added. The mixture is slowly agitated for 72 hours at room temperature.

The liquid phase is separated and the multicapillary rods are repeatedly washed with methylene chloride, methanol, 90% methanol and water. 20 mL of 0.02 M ethyl(dimethylaminopropyl)-carbodiimide in 0.1 M 2-morpholinoethanesulfonic acid buffer, pH 4.5, is added, and the mixture is slowly agitated for one hour at room temperature. The liquid phase is separated, and 5 mL of the 5 μg/mL solution of ricin antibody in 0.1 M phosphate buffered saline, pH 7.2, is added. The mixture is slowly agitated for two hours at room temperature. The liquid phase is separated. The multicapillary rods are repeatedly washed with phosphate buffered saline, pH 7.2, then washed with water and stored at 4° C.

Example 27

Polypropylene Pipette Tip Format Multicapillary Sample Preparation Device

A 1 mm to 5 mm outer diameter multicapillary element 10, prepared as described in Example 6, is tightly pushed to the lower end of a polypropylene 10 μL to 5,000 μL volume micropipette tip. The lower portion of the pipette tip is placed for ten minutes in an oven thermostated at a temperature at which polypropylene begins to soften. Polypropylene pipette tip format multicapillary devices for sample preparation 12, 20 are shown in FIGS. 4A and 4B.

Example 28

Polyethylene Pipette Format Multicapillary Sample Preparation Device

A 1 mm to 5 mm outer diameter multicapillary element 10, prepared as described in Example 6, is tightly placed in the lower end of a disposable polyethylene transfer pipette. The lower portion of the pipette is placed for ten minutes in an oven thermostated at a temperature at which polyethylene begins to soften. A polyethylene pipette format multicapillary device for sample preparation 12, 20 is shown in FIG. 4C.

Example 29

Syringe Format Multicapillary Sample Preparation Device #1

A 2 mm outer diameter multicapillary element 10, prepared as described in Example 5, is attached to a heat shrinkable tubing. A removable syringe needle is attached to the second end of the heat shrinkable tubing. The heat shrinkable tubing zone is heated at a temperature recommended for the shrinkable tubing for ten minutes A representative syringe format multicapillary device for sample preparation 12, 22 is shown in FIG. 5A.

Example 30

Syringe Format Multicapillary Sample Preparation Devices #2 and #3

A 2.3 mm outer diameter multicapillary element 10, prepared as described in Example 5, is tightly placed in a removable thermoplastic syringe hub. The hub is heated for ten minutes in an oven thermostated at a temperature at which thermoplastic begins to soften. Syringe format multicapillary devices for sample preparation 12, 22 are shown in FIGS. 5B and 5C.

Example 31

Separation of Three Component Mixture

A three component mixture (uracil, fluorene, and phenanthrene) is separated on the multicapillary device for sample preparation prepared as described in Example 5 and installed on a model LC-600 Shimadzu liquid chromatographic instrument using standard HPLC fittings. The chromatographic conditions and chromatogram are reproduced in FIG. 6. The chromatogram shows a uracil peak at about 1.8 minutes, a fluorene peak at about 2.1 minutes, and a phenanthrene peak at about 2.4 minutes. The example illustrates a liquid chromatographic application using the multicapillary device for sample preparation of the present invention, which enables a typical organic mixture to be analyzed in less than three minutes.

Example 32

Sample Enrichment for HPLC Analysis

Referring to FIG. 7A, a 2.3 mm outer diameter×100 mm length multicapillary C-18 device for sample preparation containing approximately 1,400 capillaries of 40 μm diameter prepared as described in Example 5 is used for sample enrichment prior to HPLC analysis. At present, short HPLC columns known as solid phase extraction ("SPE") cartridges are commonly used for sample preparation. Compared to SPE cartridges, multicapillary devices for sample preparation 12 are much faster, simpler and reusable. Performance of the present multicapillary device for sample preparation 12 (FIG. 7A) as compared to a standard SPE cartridge (FIG. 7B) is shown in Table 1.

TABLE 1

Multicapillary Device vs. Conventional SPE Cartridge.

| | Characteristics | SPE Cartridge | Multicapillary Device |
|---|---|---|---|
| 1 | Collection time | 20-40 minutes | 1-5 minutes |
| 2 | Amount | 1-5 ml samples | 100-200 μl samples |
| 3 | Processing the extract | Extract volume 5-20 ml Requires evaporation for analysis | No concentration or evaporation of the extract required |
| 4 | Reconditioning | Cannot be reconditioned | Reconditioned by washing with methanol and water for 2 min. |
| 5 | Reusability | Cannot be reused | Can be reused at least 50-100 times depending on the sample to be extracted |

TABLE 1-continued Multicapillary Device vs. Conventional SPE Cartridge.

| | Characteristics | SPE Cartridge | Multicapillary Device |
|---|---|---|---|
| 6 | Silica particles in the sample | Fine silica particles in the samples | No silica or other particles in the samples |
| 7 | Auto samplers adaptability | Cannot be used in auto samplers | Easily adaptable to auto samplers |
| 8 | Field use | Difficult to transport Costly equipment/ accessories | Requires only syringes |

Example 33

Hydrolysis of Bovine Serum Albumin

A 10 µL volume of 0.25 mg/mL bovine serum albumin solution in a 40:60 mixture of acetonitrile and 0.2 mM ammonium bicarbonate, pH 7.5, is aspirated in the multicapillary sample preparation device, prepared as described in Example 24, and thermostated at 37° C. After five minutes, the digested sample is dispensed in a vial and stored at 4° C.

Example 34

Desalting of Peptide Samples

Figure 8A:
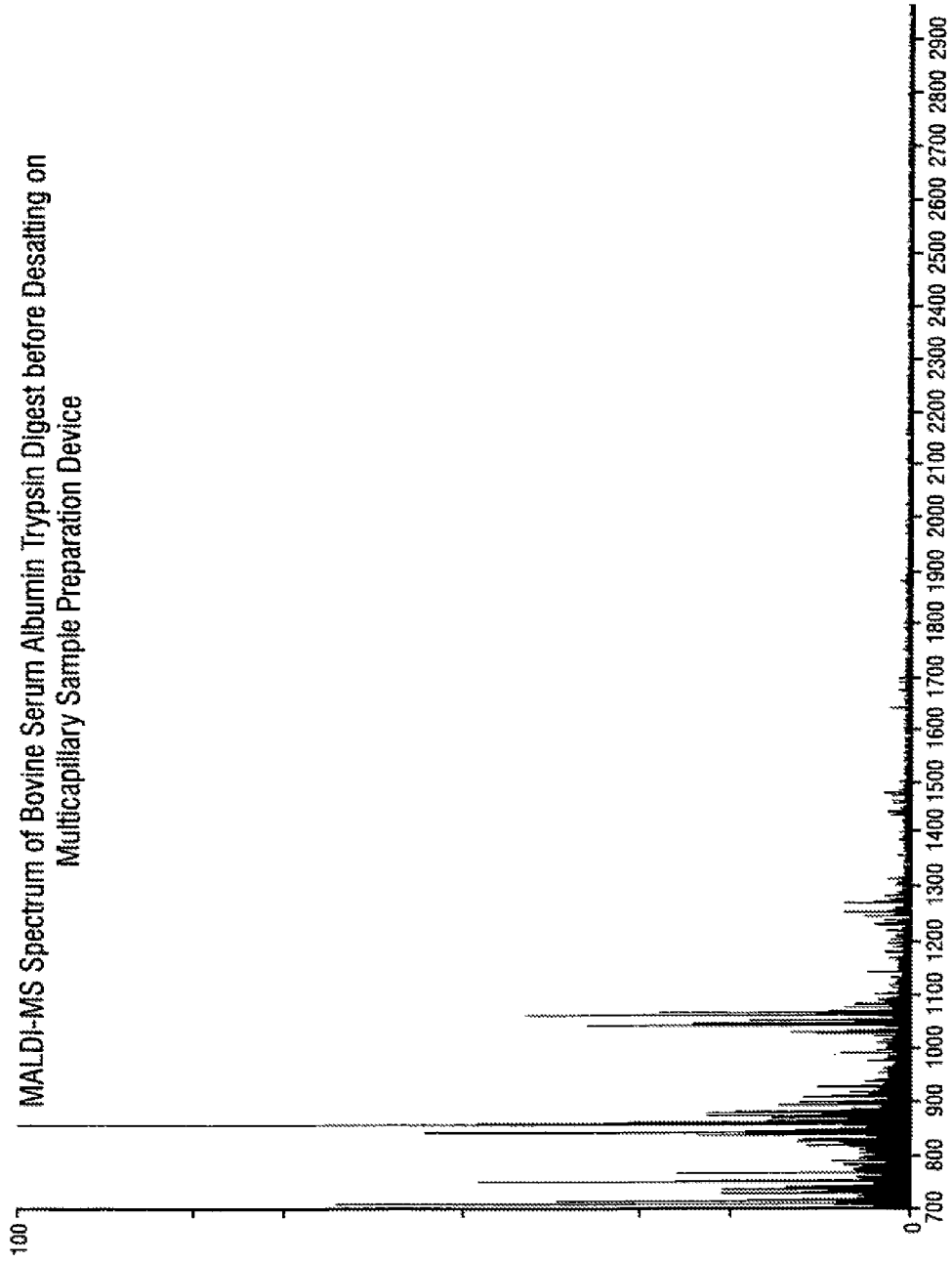
FIGS. 8A and 8B are mass spectra demonstrating the performance of a multicapillary sample preparation device in desalting of complex peptide mixtures.
Figure 8B:
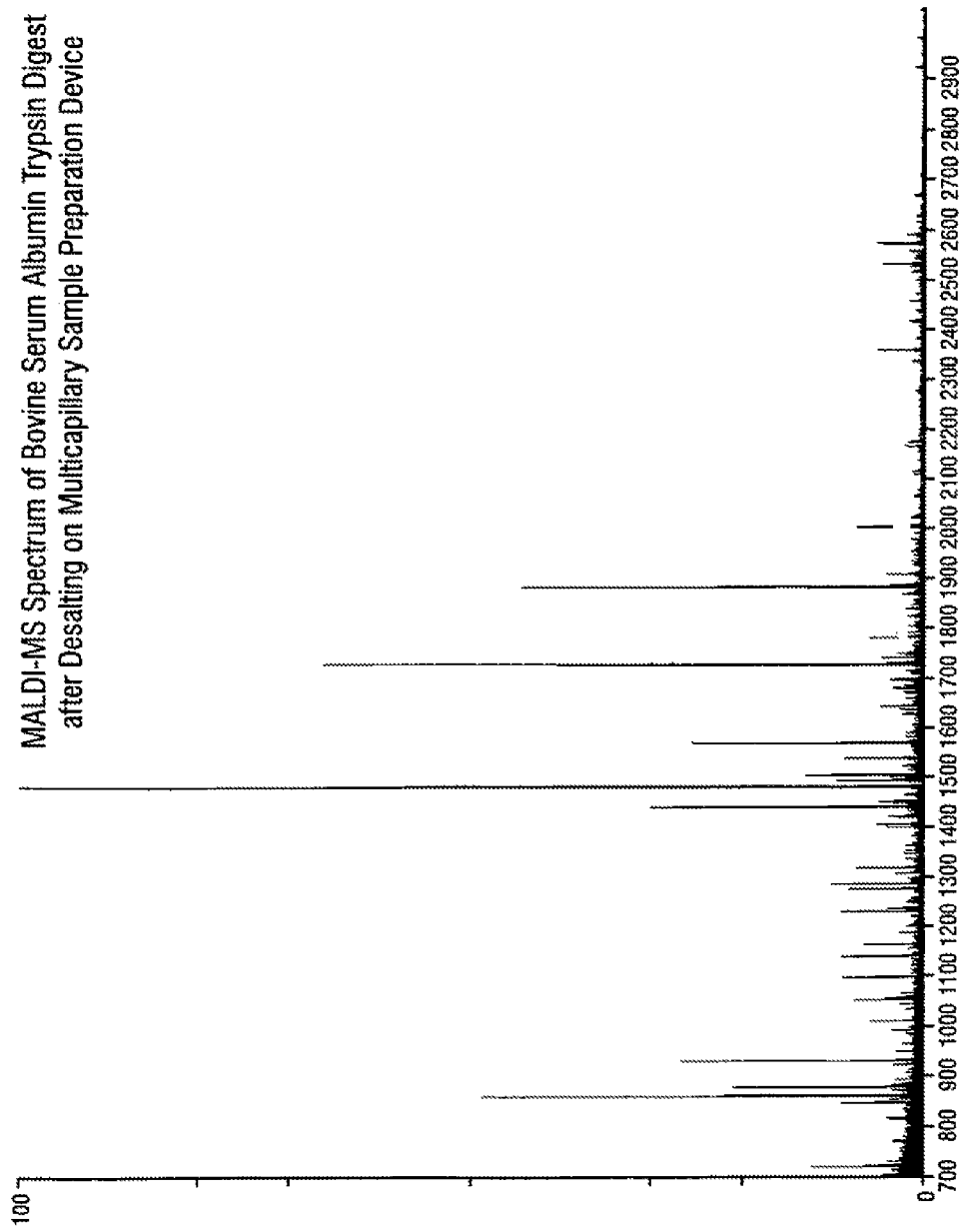

The bovine serum albumin digest, prepared as described in Example 34, is dried with a nitrogen stream and dissolved in 10 µL of 0.1% trifluoroacetic acid (TFA) in water. 1 µL of this sample is aspirated and dispensed from the multicapillary sample preparation device, as described in Examples 5 and 27. Three 10 µL portions of 0.1% trifluoroacetic acid (TFA) in 5% acetonitrile/water are pumped in and out of the multicapillary sample preparation device. The sample is eluted from the multicapillary sample preparation device with a 5 µL portion of 0.1% TFA in 70% acetonitrile/water and analyzed by MALDI-MS. The MALDI-MS spectra of the sample before and after desalting are shown in FIGS. 8A and 8B.

Example 35

Fractionating of Peptides

Figure 9A:
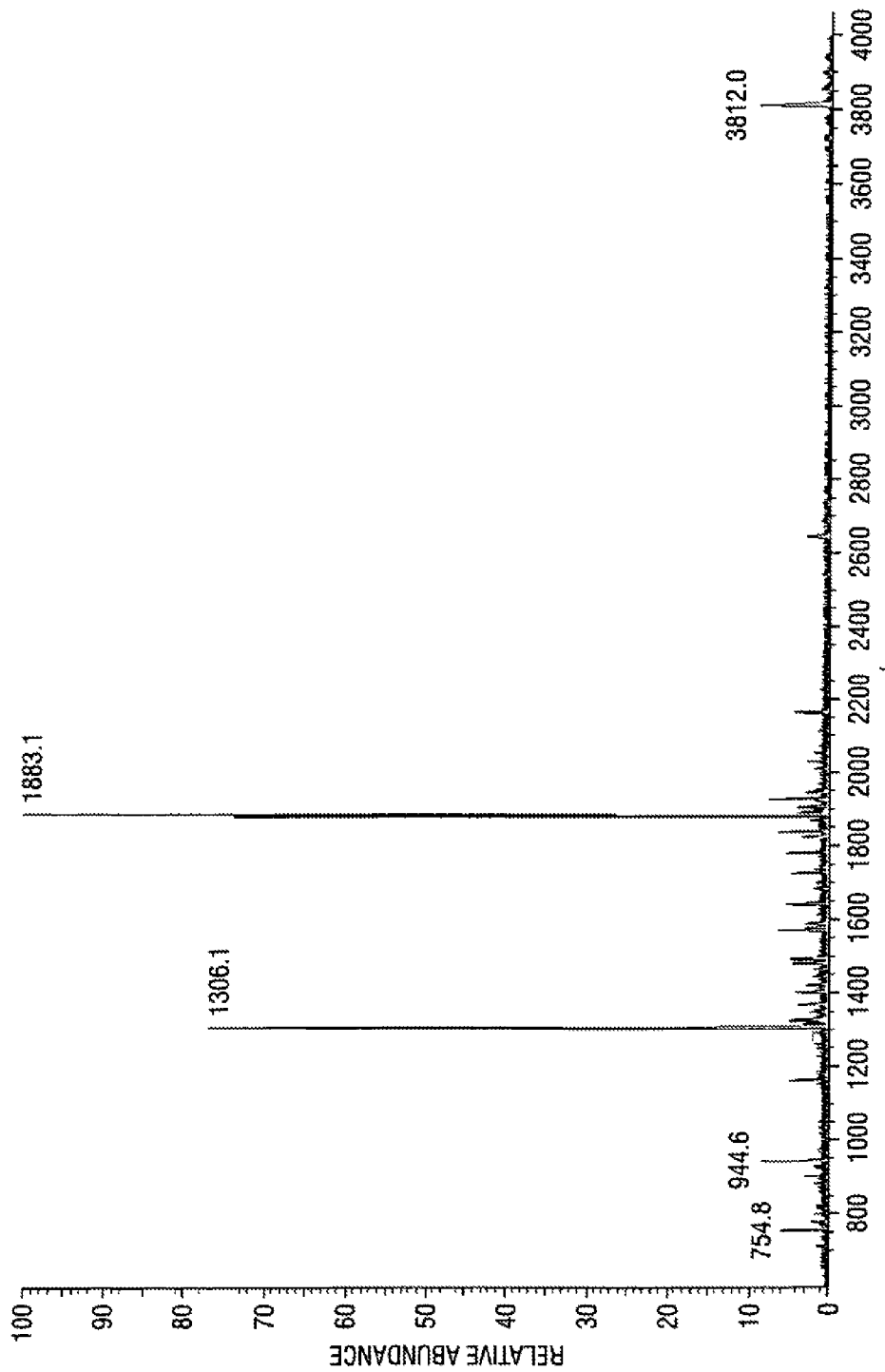
FIGS. 9A and 9B are mass spectra demonstrating the performance of a multicapillary sample preparation device in fractionating of complex peptide mixtures.
Figure 9B:
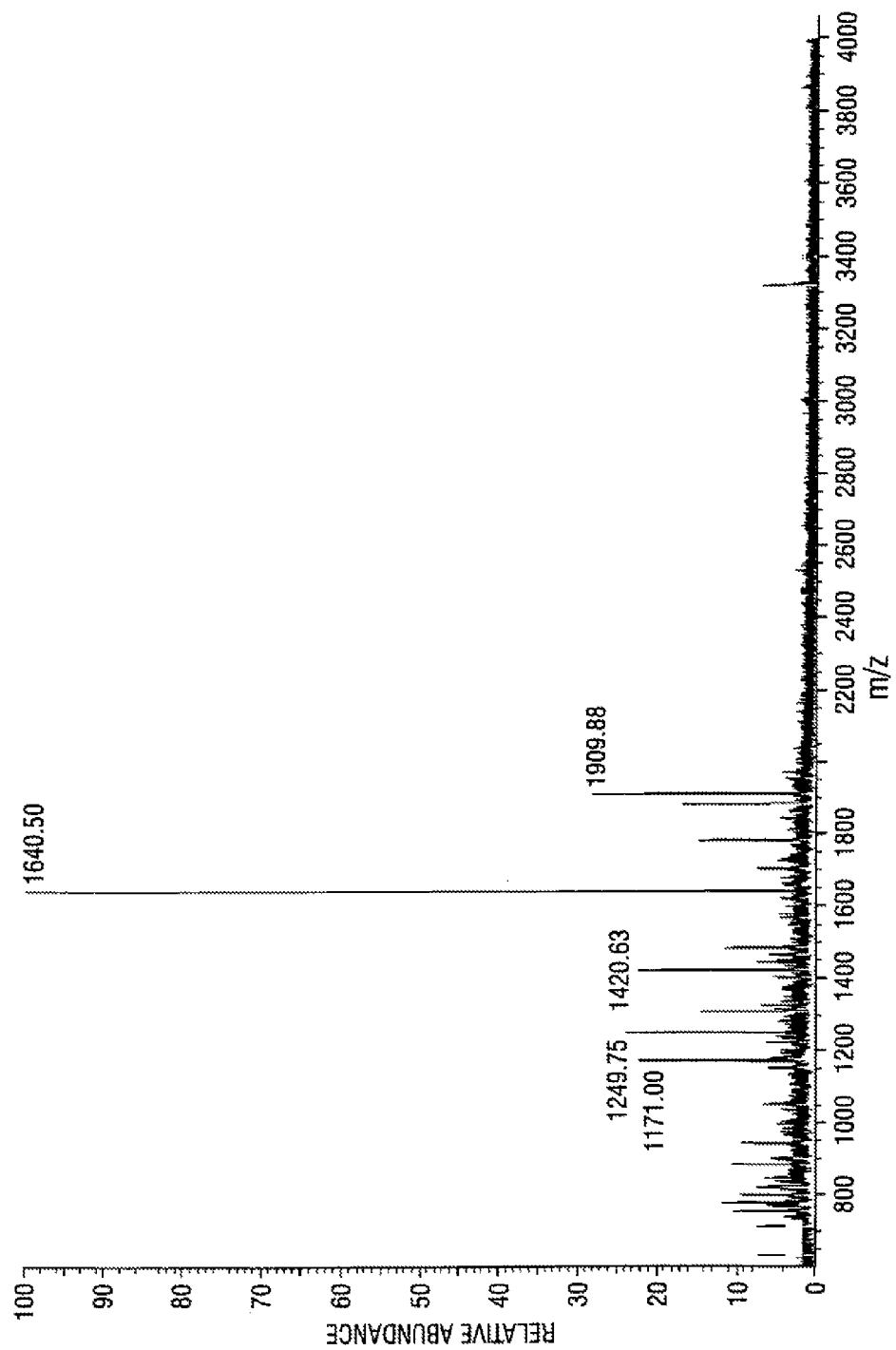

A 3 µL volume of the 100 pmole/µL peptide mixture obtained by the enzymatic hydrolysis of bovine serum albumin, as described in Example 34, is introduced into a 10 cm long C-18 multicapillary sample preparation device. The sample is eluted at 100 µL/min with 100 µL of 0.1% TFA in water followed by 30 µL of 0.1% TFA in 40% acetonitrile/water. Ten 3 µL 40% acetonitrile/water fractions are collected and analyzed by MALDI-MS. The mass-spectra of fractions 3 and 6 are shown in FIGS. 9A and 9B. This example illustrates the fractionating ability of the multicapillary sample preparation device of the present invention, prior to MALDI-MS analysis of a complex peptide mixture.

Example 36

Gel Electrophoresis of Proteins

Figure 10A:
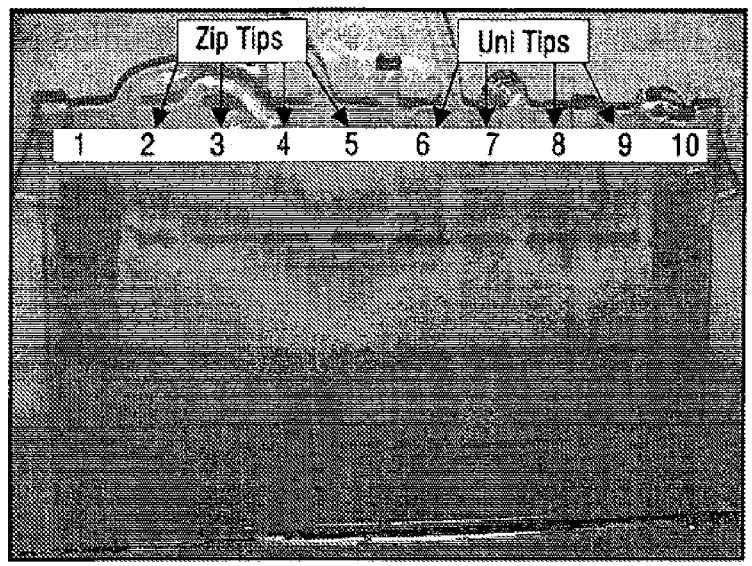
FIG. 10 shows gels demonstrating sample capacity and recovery performance (10A), reproducibility (10B), and time performance (10C) of a conventional device versus a multicapillary sample preparation device according to the present invention. Comparative data is shown in Table 2.
Figure 10B:
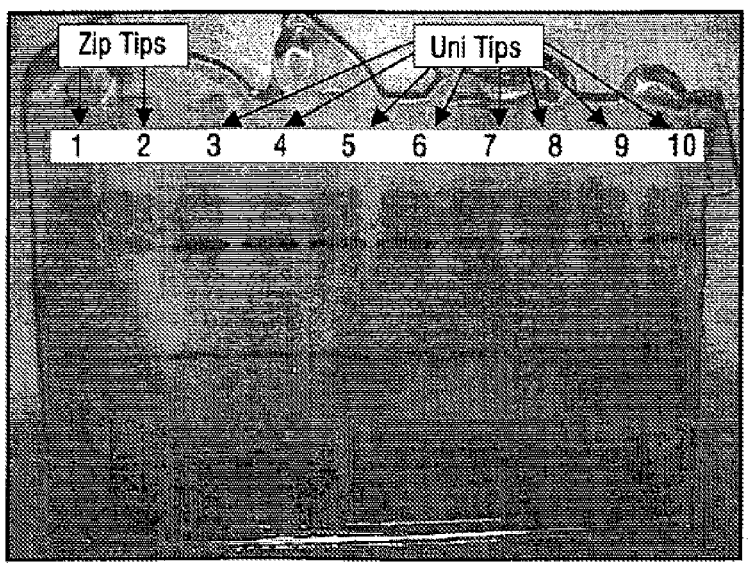

FIGS. 10A and 10B depict gels produced to evaluate the sample capacity, recovery, and reproducibility of a multicapillary device for sample preparation according to the present invention, as compared to commercially available porous silica-based devices. Lanes 1 and 10 are protein standards inserted for purposes of comparison. Lanes 2 to 5 represent the conventional devices, while Lanes 3 to 10 denote the multicapillary sample preparation device of the instant invention.

The test sample used for electrophoresis is a mixture of the following four representative proteins: Phosphorylase B (MW 97,400), Bovine Serum Albumin (MW 66,200), Carbonic Anhydrase (MW 31,000), and Lysozyme (MW 14,400). These proteins were selected due to their varying size and generally known properties. Moreover, these proteins are commonly used as standards. All results were reproduced and retested several times to ensure accuracy. Testing was conducted at ChromBA, Inc. (State College, Pa.), The Materials Research Institute (University Park, Pa.), The Milton Hershey Medical Center (Hershey, Pa.), Huck Institute (University Park, Pa.), APD LifeSciences Inc. (State College, Pa.), and MassTech Inc. (Columbia, Md.). In total, over 40 gels were used, including both $C_{18}$ and $C_4$, the two most popular phases on the market. In addition, more than 500 sample preparation devices were tested.

In both figures, the conventional silica-based devices (FIG. 10A: Lanes 2-5; FIG. 10B: Lanes 1-2) show faint and varying bands. In contrast, the device of the present invention (FIG. 10A: Lanes 6-9; FIG. 10B: Lanes 3-10) shows bold and dark bands, indicating vastly superior binding capacity, and recovery. Moreover, the bands of the present device are clearly more identical from lane to lane demonstrating superior reproducibility. As shown in Table 2, further quantification reveals that the sample preparation device of the present invention, on average, binds and releases nearly twice the protein bound and released by conventional devices, and demonstrates half the margin of error (i.e., variance in amount of sample bound).

TABLE 2

Sample Capacity, Recovery Performance, and Reproducibility of Multicapillary Device vs. Conventional Devices.

| | | MEAN VALUE OF BAND INTENSITY | | % OF INCREASED CAPACITY | AVERAGE MARGIN OF ERROR | |
|---|---|---|---|---|---|---|
| | PROTEIN | Convent. Device | Multicap. Device | Multicap. Device | Convent. Device | Multicap. Device |
| FIG. 10A | Phosphorylase B | 45.7 | 56.2 | 23% | 5.8% | 3.4% |
| | Bovine Serum Albumin | 85.2 | 162.1 | 91% | | |
| | Carbonic Anhydrase | 86.8 | 131.4 | 51% | | |
| | Lysozyme | 84.2 | 151.6 | 79% | | |

TABLE 2-continued

Sample Capacity, Recovery Performance, and Reproducibility of Multicapillary Device vs. Conventional Devices.

|  | PROTEIN | MEAN VALUE OF BAND INTENSITY | | % OF INCREASED CAPACITY | AVERAGE MARGIN OF ERROR | |
|---|---|---|---|---|---|---|
|  |  | Convent. Device | Multicap. Device | Multicap. Device | Convent. Device | Multicap. Device |
| FIG. 10B | Phosphorylase B | — | — | — | — | — |
|  | Bovine Serum Albumin | 85.5 | 135.1 | 107% | 6.3% | 3.8% |
|  | Carbonic Anhydrase | 70.1 | 108.6 | 55% |  |  |
|  | Lysozyme | 77.0 | 157.6 | 104% |  |  |

Figure 10C:
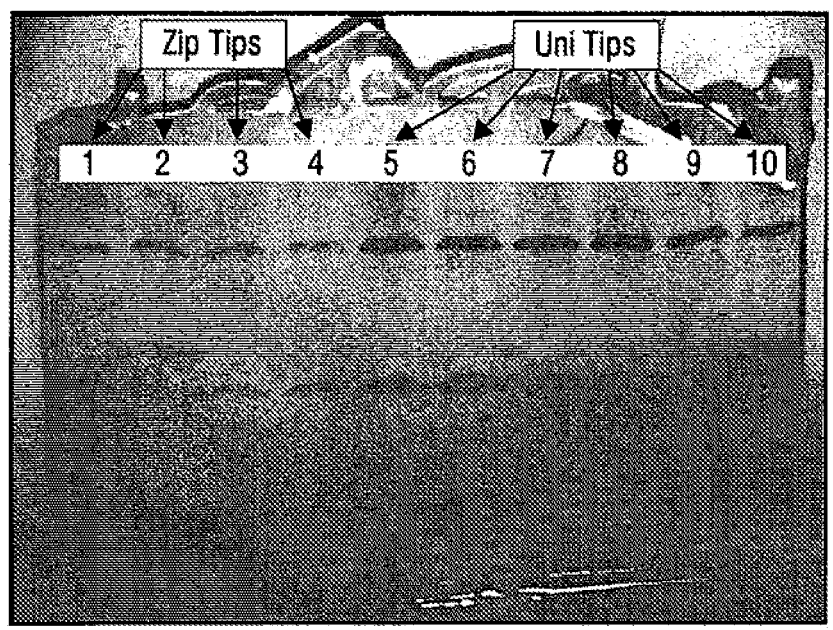

FIG. 10C shows a gel produced to evaluate the speed of use (time performance) of a multicapillary device for sample preparation according to the present invention relative to commercially available silica-based devices. As recommended by the manufacturers, a sample must be passed through the tip of the silica-based devices approximately ten times to achieve suitable results. This is largely due to the fact that most of the sample travels through large voids in the filtration material and is subsequently not adsorbed and cleaned. Specifically, as illustrated by Lanes 1-4 of FIG. 10C, the conventional devices show faint bands even after ten passes through the tip.

In contrast, Lanes 5-10 show nearly identical spots for samples passed through the multicapillary device of the present invention only once. Notably, the bands are much darker and broader than those of the silica-based devices, denoting the presence of vastly greater amounts of protein.

Figure 11A:
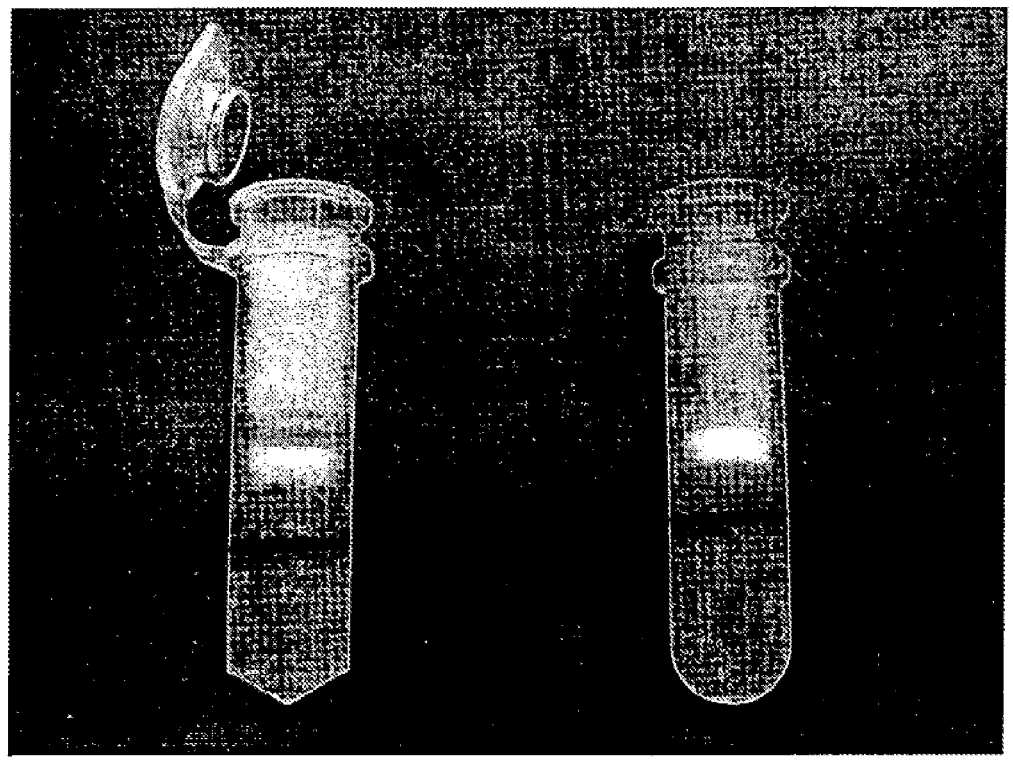
FIG. 11A is a perspective view of a conventional spin column used for DNA purification.
Figure 11B:
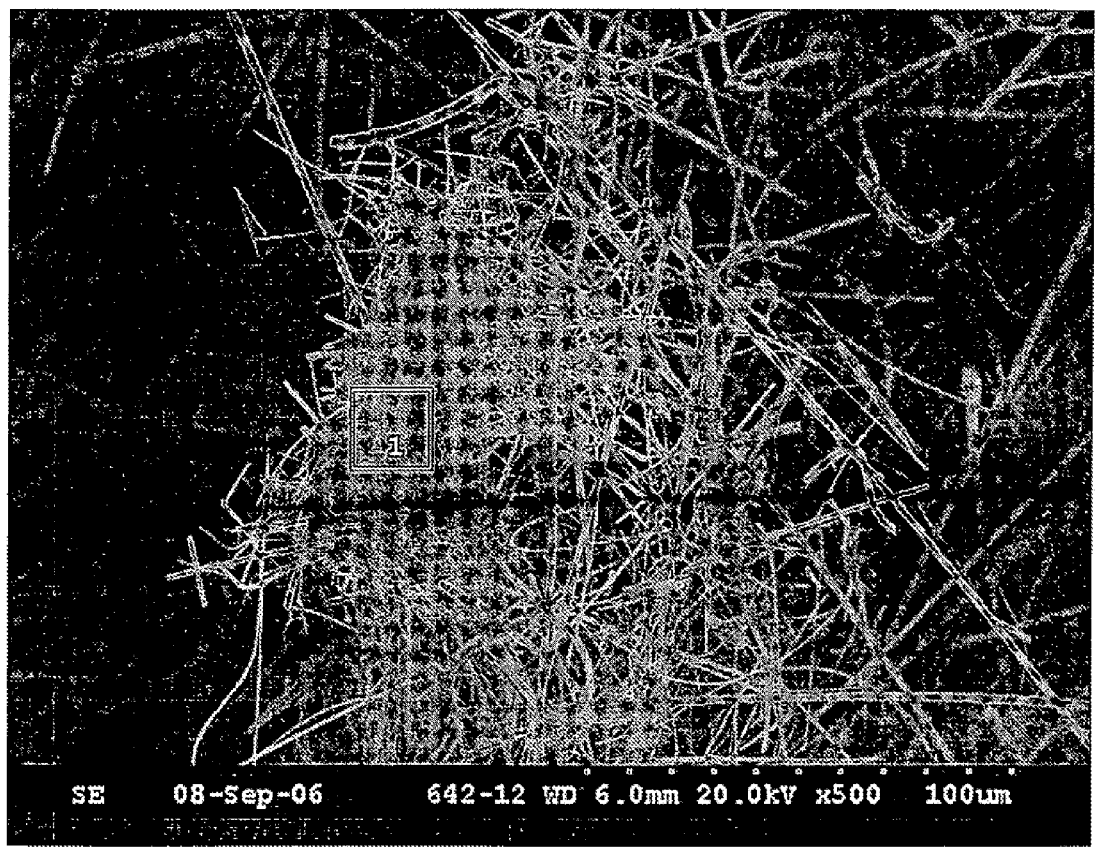
FIGS. 11B and 11C are SEM images of the spin column.
Figure 11C:
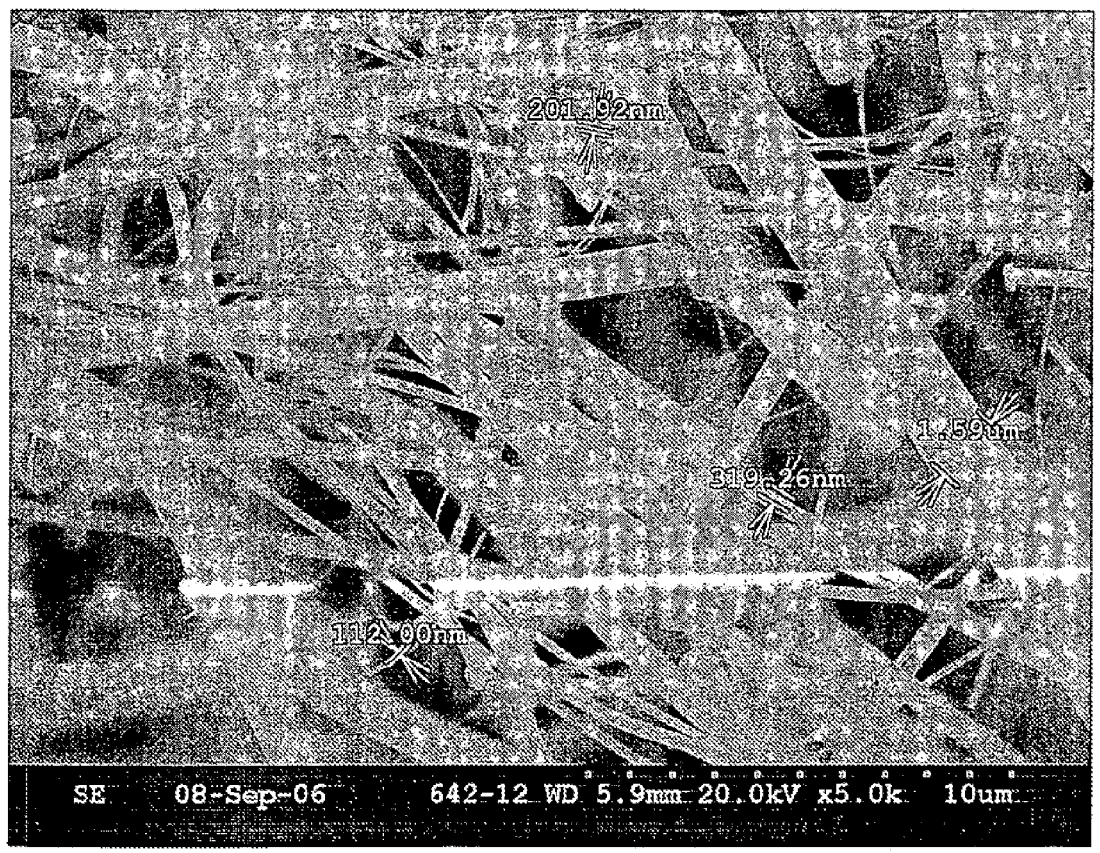

In FIGS. 10A-10C, the darkness and size of the bands on the gels developed by electrophoresis indicate the amount of protein bound by and recovered from the sample preparation devices; namely, pipette tips with integral silica-based plugs versus multicapillary elements. The superior performance of the multicapillary device 12 of the present invention is due, in part, to the uniform, consistent and virtually identical pathways for sample passage through the device, along with excellent tip-to-tip duplication, as shown in FIG. 2. FIG. 3 and FIG. 11, in contrast, depict cross-sections of commercially available (market leader) porous silica and silica fiber based sample preparation devices. The silica based devices reveal irregular particle sizes and fiber diameter, large voids (dark areas), and vastly different sample pathways. Moreover, the conventional devices demonstrate poor tip-to-tip duplication (i.e., tremendous variance).

Example 37

Isolation of Nucleic Acids

The following experiments, featuring both syringe 22 and pipette tip 20 format multicapillary devices 12, demonstrate the advantage of using a multicapillary device for sample handling and extraction of DNA from various biological samples, such as tissue, blood, bacterial cells, urine, etc.

A multicapillary device for sample preparation 12 (1 to 2.5 mm outer diameter, 0.25 to 3 cm long, approximately 4000 capillaries of 10 to 40 μM diameter, inner volume 2 to 90 μL) is loaded twice with 10 to 1,000 μL lysed biological sample. After discarding the loading solution, the multicapillary device 12 is rinsed with a washing buffer to dispose of proteins and other non-DNA type materials. Adsorbed DNA is then eluted with 10 to 300 μL elution buffer. The eluted DNA is analyzed using a variety of methods including Yo-Pro fluorescence on a Packard FluoroCount instrument at 530 nm (for yield determination), Agarose gel electrophoresis (for quality determination), and pulsed field gel electrophoresis (for DNA size and quality determination).

Figure 13A:
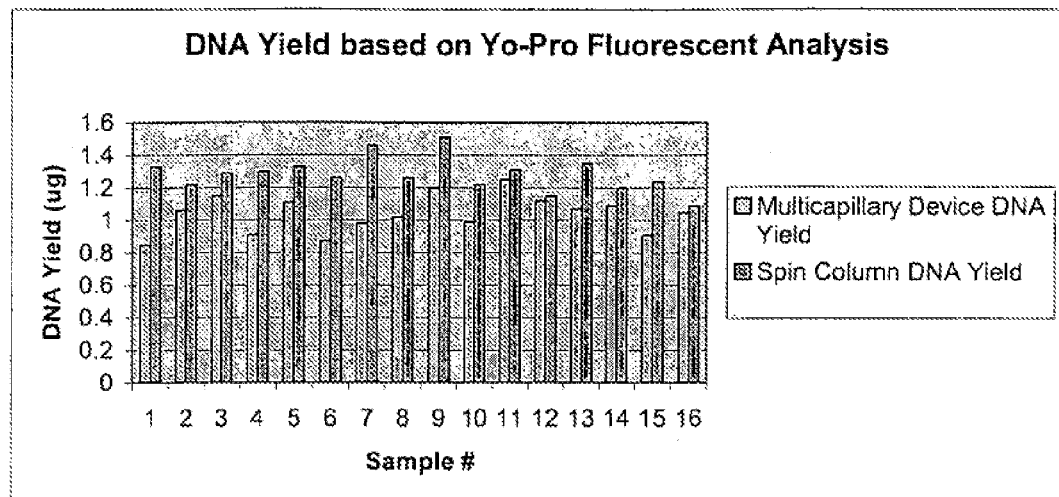
FIGS. 13A and 13B, respectively, show sample purification results of conventional spin columns versus a multicapillary sample preparation device of the present invention in terms of DNA yield and time required for sample preparation
Figure 13B:
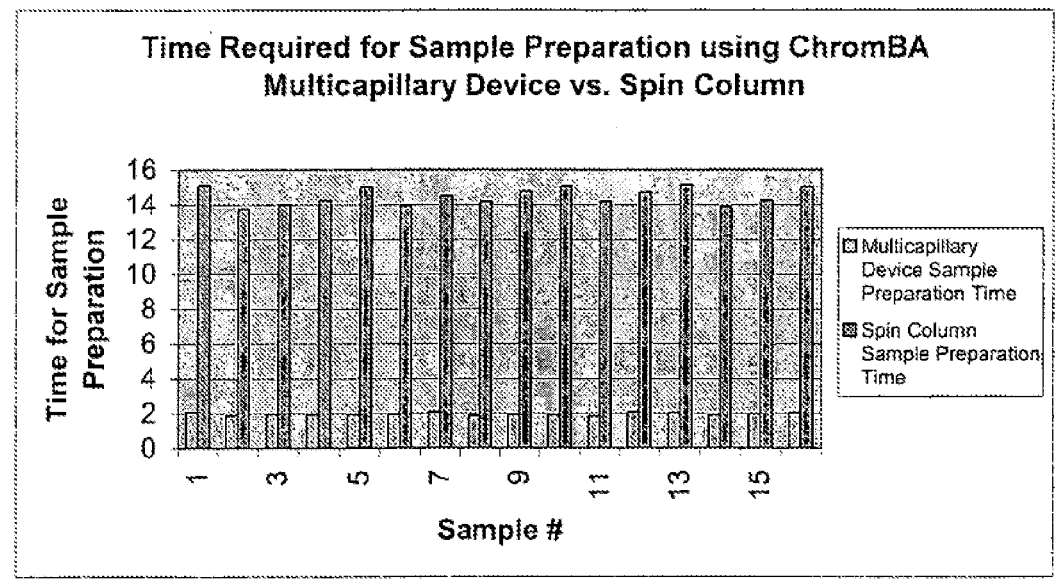

FIGS. 13A and 13B, respectively, are bar graphs comparing 16 rat liver samples' purification results in terms of DNA yield and time required for sample preparation using 25 μm×1 cm×200 μL pipette tip format multicapillary devices 12, 20 according to the present invention and 16 commercially available (market leader) spin columns. The data for DNA yield was obtained using Yo-Pro fluorescence, and time was recorded with a stopwatch for each sample. The experiments demonstrate that the multicapillary devices 12 of the present invention are comparable to conventional spin columns in terms of DNA yield, but require significantly less time for processing. Notably, use of the present multicapillary devices results in a seven-fold decrease in "hands-on" labor time for DNA isolation sample preparation.

Figure 12A:
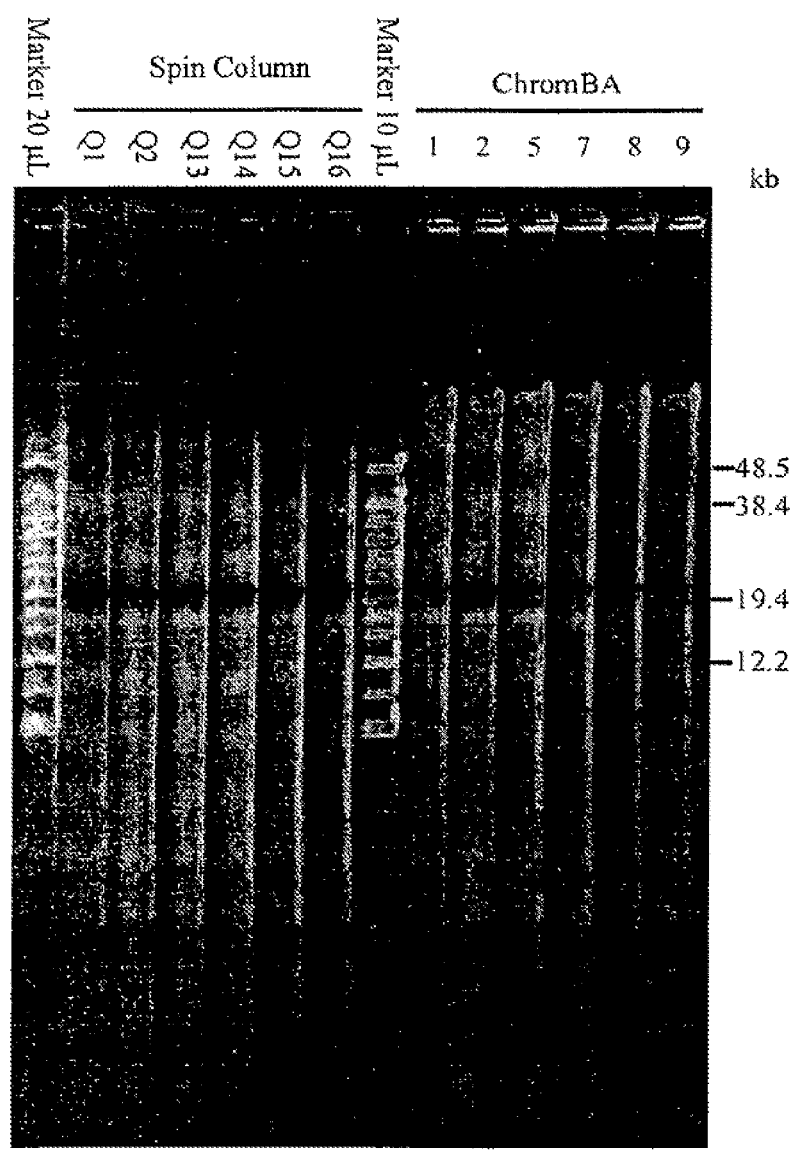
FIGS. 12A and 12B, respectively, show pulsed field and agarose gel electrophoresis analyses performed to determine DNA quality and size of a conventional spin column versus a multicapillary sample preparation device according to the present invention.
Figure 12B:
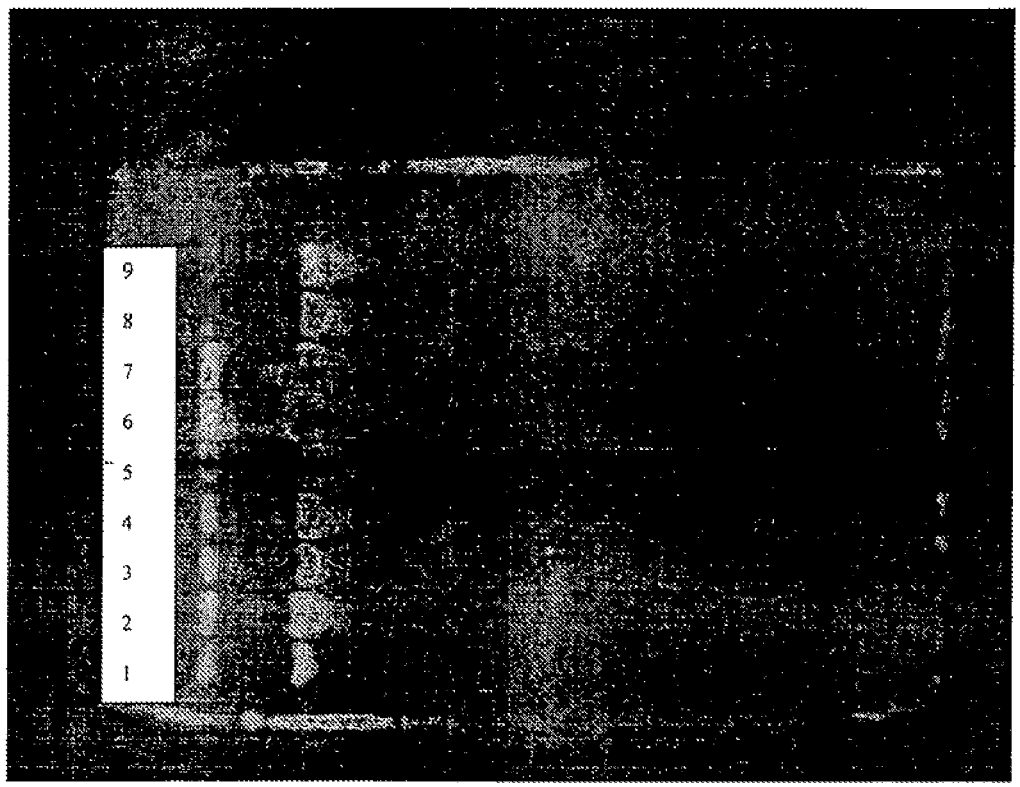

Agarose gel electrophoresis and pulsed field gel electrophoresis analyses were performed to determine DNA quality and size. FIG. 12B shows a 0.8% agarose gel run to analyze DNA extracted from whole bovine blood using the pipette tip format multicapillary devices (Lanes 1-7) and commercially available spin columns (Lanes 8-9), demonstrating comparable DNA yields and quality. Further, as shown in FIG. 12A, pulsed field gel electrophoresis was used to size DNA strands of purified samples using the multicapillary device 12 of the present invention and commercially available spin columns. As compared to the leading spin columns, samples extracted using the present multicapillary device 12 demonstrate considerably larger DNA fragments, which suggests a significant decrease in DNA breakage or "shearing" during sample processing. Larger fragments of DNA reflect a better quality of the purified sample, which is highly desirable for many downstream applications such as PCR and sequencing.

As demonstrated in FIGS. 12 and 13, significant DNA shearing is unavoidable in specimens processed using the commercially available spin columns, which are operated by means of a centrifuge. In the multicapillary device 12 of the present invention, however, DNA shearing is largely avoided through the use of an insoluble, surface-mediated mechanism of separation, which ensures that capillary channels (lumens) remain open and unobstructed throughout sample processing. Use of a gentle pipetting procedure for sample processing, in lieu of the commonly employed centrifuge, further contributes to the quality and size of DNA processed by means of the multicapillary devices 12 disclosed herein.

Table 3 shows the absorbance reading of five multicapillary devices 12 prepared according to the method described above. The average DNA recovery yield is 50-60%, which demonstrates that the multicapillary device for sample preparation 12 is efficacious for sample handling, purification and isolation of nucleic acids.

TABLE 3

DNA Isolation on Multicapillary Device.

| Sample | Fluorescence Reading (Units) |
|---|---|
| Blank elution buffer | 21 |
| Elution buffer spiked with 16 µg/mL DNA | 214 |
| Eluted DNA from MC | 211 |
| Eluted DNA from MC | 211 |
| Eluted DNA from MC | 217 |
| Eluted DNA from MC | 238 |
| Eluted DNA from MC | 213 |

Example 38

Sample Handling of Cells

To demonstrate the use of a multicapillary device 12 for sample handling of cells, the following cells are grown and evaluated: mouse myeloma Sp2/0-Ag14, approximately 25 µm size; mouse macrophage J774A1, approximately 15 µm size; and human prostrate tumor THP-1 approximately 20 µm size. A syringe format multicapillary device for sample preparation 12, 22 (2.3 mm outer diameter, 150 mm long, approximately 1400 capillaries of 40 µm diameter, inner volume 262 µL) is attached to a syringe and rinsed with 1 mL of balanced salt solution creating an environment conductive to cell viability. At room temperature, a 1.5-3.0 mL volume of cell suspension is passed through the multicapillary device at a flow rate of 1 mL/min, followed by a 0.5 mL volume of balanced salt solution. The eluted cell suspension is concentrated by centrifugation and cells are counted using a hemacytometer. The change in cell viability after passage through the multicapillary device is presented in Table 4.

TABLE 4

Cell Viability Upon Passage Through Multicapillary Device.

| Cell | Suspension Volume | Concentration of Cells | Viable Cells Initial | Viable Cells Recovered | % Viable Cells Recovered |
|---|---|---|---|---|---|
| Sp2/0-Ag14 | 3.0 mL | $1 \times 10^6$ cells/mL | $2.73 \times 10^6$ | $2.09 \times 10^6$ | 76.5 |
| J774A1 | 2.0 mL | $3.5 \times 10^6$ cells/mL | $6.30 \times 10^6$ | $3.57 \times 10^6$ | 56.6 |
| THP-1 | 2.0 mL | $3.5 \times 10^6$ cells/mL | $6.65 \times 10^6$ | $5.06 \times 10^6$ | 76.1 |

The data reveal that the vast majority of each cell type passed through the device emerges unharmed. Therefore, the multicapillary device for sample preparation is highly efficacious for sample handling of cells.

Manufacturers of existing pipette tips state in their technical literature that 40-60% sample loss is average for a purified product. In comparison, the increased capacity and recovery afforded by the present invention substantially reduces and/or eliminates the critical problem of sample loss in the pipette tip. Moreover, equipment wear is reduced, since the present invention eschews repeat sample passage, as required by conventional silica-based devices.

As demonstrated by the foregoing Examples 1-38, the multicapillary device 12 of the present invention enables a user to achieve superior sample preparation results in significantly less time. Indeed, the device's 12 ability to return quality results quickly and reproducibly permits a user to increase the throughput of available sample preparation stations at least several times, depending upon the sample and system employed.

In short, the multicapillary sample preparation device 12 of the present invention advantageously increases sample throughput and decreases variance in a highly reproducible fashion. The multicapillary device 12 may be used in an array of applications without departing from the scope of the invention. These include, but are not limited to, sample handling of small molecules, polymers, viruses and cells; the isolation, purification, concentration, desalting and fractionation of biological samples and nucleic acids, including DNA and RNA; solid phase extraction; head space analysis; gas chromatography; liquid chromatography (e.g., HPLC); supercritical chromatography; electrochromatography; and capillary electrophoresis.

Representative examples of the above-mentioned applications include: sample preparation of biological samples such as proteins, peptides, and polynucleotides, fractionation of peptide mixtures prior to mass-spectrometric analysis, desalting of samples prior to instrumental analysis, desalting of peptide solutions, desalting of protein solutions, sample concentration prior to instrumental analysis, and peptide concentration prior to mass-spectrometric analysis.

While the invention has been particularly shown and described with reference to the examples and preferred embodiments thereof, it will be understood by those skilled in the art that various alterations in form and detail may be made therein without departing from the spirit and scope of the invention.

What is claimed is:

1. A method for isolating nucleic acid, comprising:
   (a) loading a multicapillary element retained in or attached to a pipette, micropipette, pipette tip, or syringe device, with a loading solution comprising nucleic acid under conditions that permit adsorption of the nucleic acid to the inner wall of the capillaries, which multicapillary element comprises a plurality of parallel capillaries comprising a substantially imperforate inner wall;
   (b) discarding the loading solution from the device after (a); and
   (c) eluting the nucleic acid from the multicapillary element after (b), whereby the nucleic acid is isolated from the loading solution.

2. The method of claim 1, wherein the device comprises a plastic, glass, fused silica, ceramic, or stainless steel.

3. The method of claim 2, wherein the plastic is formed from polyetheretherketone, polystyrene, polypropylene or polyethylene.

4. The method of claim 3, wherein the device is formed from polypropylene.

5. The method of claim 1, wherein the device is a pipette tip.

6. The method of claim 5, wherein the pipette tip is formed from polystyrene, polypropylene or polyethylene.

7. The method of claim 6, wherein the pipette tip is formed from polypropylene.

8. The method of claim 1, wherein the capillaries are substantially cylindrical.

9. The method of claim 1, wherein the cross section of the capillaries is substantially polygonal.

10. The method of claim 1, wherein the cross section of the capillaries is substantially hexagonal.

11. The method of claim 1, wherein the multicapillary element comprises fused silica, glass, ceramic, stainless steel, polystyrene, polypropylene, polyethylene, or polyetheretherketone.

12. The method of claim 11, wherein the multicapillary element consists of fused silica.

13. The method of claim 11, wherein the multicapillary element consists of glass.

14. The method of claim 1, wherein an inner diameter of each capillary is about 0.1 micrometers to about 200 micrometers.

15. The method of claim 1, wherein an outer diameter of the multicapillary element is about 1 mm to about 20 mm.

16. The method of claim 1, wherein the length of the multicapillary element is about 1 mm to about 250 mm.

17. The method of claim 1, wherein the volume of the device is about 1 microliter to about 100 microliters.

18. The method of claim 1, wherein the inner wall of the capillaries includes particles of inert material.

19. The method of claim 1, wherein the inner wall of the capillaries includes a nodular surface.

20. The method of claim 1, wherein the inner wall of the capillaries is etched.

21. The method of claim 1, wherein the nucleic acid comprises deoxyribonucleic acid (DNA).

22. The method of claim 1, wherein the nucleic acid comprises ribonucleic acid (RNA).

23. The method of claim 1, wherein the nucleic acid isolated is sheared less than nucleic acid isolated from a device that includes porous silica.

24. The method of claim 1, further comprising washing the multicapillary element after the loading solution is discarded and before the nucleic acid is eluted from the multicapillary element.

25. The method of claim 1, wherein the inner surface of each capillary comprises an insoluble stationary phase coated directly on the inner wall of the capillaries.

26. The method of claim 25, wherein the stationary phase comprises C18.

* * * * *